(12) United States Patent
Dahl et al.

(10) Patent No.: US 8,871,271 B2
(45) Date of Patent: Oct. 28, 2014

(54) METHOD AND COMPOSITION FOR PHARMACEUTICAL PRODUCT

(71) Applicant: Gilead Sciences, Inc., Foster City, CA (US)

(72) Inventors: Terrence C. Dahl, Sunnyvale, CA (US); Mark M. Menning, San Francisco, CA (US); Reza Oliyai, Burlingame, CA (US); Taiyin Yang, Monte Sereno, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/953,577

(22) Filed: Jul. 29, 2013

(65) Prior Publication Data

US 2014/0037732 A1    Feb. 6, 2014

Related U.S. Application Data

(63) Continuation of application No. 11/452,472, filed on Jun. 13, 2006, now abandoned.

(60) Provisional application No. 60/690,010, filed on Jun. 13, 2005, provisional application No. 60/771,353, filed on Feb. 7, 2006.

(51) Int. Cl.
| | |
|---|---|
| *A61J 3/00* | (2006.01) |
| *A61K 31/675* | (2006.01) |
| *A61K 31/513* | (2006.01) |
| *A61K 9/20* | (2006.01) |
| *A61K 9/24* | (2006.01) |
| *A61K 31/535* | (2006.01) |
| *A61K 9/16* | (2006.01) |

(52) U.S. Cl.
CPC ............... *A61J 3/00* (2013.01); *A61K 31/675* (2013.01); *A61K 31/513* (2013.01); *A61K 9/2077* (2013.01); *A61K 9/2095* (2013.01); *A61K 9/209* (2013.01); *A61K 9/1694* (2013.01); *A61K 31/535* (2013.01)
USPC ........................................................ 424/489

(58) Field of Classification Search
USPC ........................................................ 424/464
See application file for complete search history.

(56) References Cited

U.S. PATENT DOCUMENTS

| | | |
|---|---|---|
| 3,524,846 A | 8/1970 | Moffatt et al. |
| 3,622,677 A | 11/1971 | Short et al. |
| 3,682,930 A | 8/1972 | Bourquin et al. |
| 3,994,974 A | 11/1976 | Murakami et al. |
| 4,003,878 A | 1/1977 | Skaar et al. |
| 4,258,062 A | 3/1981 | Jonas et al. |
| 4,355,032 A | 10/1982 | Verheyden et al. |
| 4,384,005 A | 5/1983 | McSweeney |
| 4,430,343 A | 2/1984 | Iemura et al. |
| 4,476,248 A | 10/1984 | Gordon et al. |
| 4,724,233 A | 2/1988 | De Clercq et al. |
| 4,808,716 A | 2/1989 | Holy et al. |
| 4,816,570 A | 3/1989 | Farquhar |
| 4,879,288 A | 11/1989 | Warawa et al. |
| 4,935,507 A | 6/1990 | Takaya et al. |
| 4,957,924 A | 9/1990 | Beauchamp |
| 4,968,788 A | 11/1990 | Farquhar |
| 5,047,407 A | 9/1991 | Belleau et al. |
| 5,075,445 A | 12/1991 | Jarvest et al. |
| 5,142,051 A | 8/1992 | Holy et al. |
| 5,151,426 A | 9/1992 | Belleau et al. |
| 5,155,268 A | 10/1992 | Hester |
| 5,177,064 A | 1/1993 | Bodor |
| 5,179,104 A | 1/1993 | Chu et al. |
| 5,204,466 A | 4/1993 | Liotta et al. |
| 5,208,221 A | 5/1993 | Kim et al. |
| 5,210,085 A | 5/1993 | Liotta et al. |
| 5,386,030 A | 1/1995 | Kim et al. |
| 5,432,172 A | 7/1995 | Kashman et al. |
| 5,466,806 A | 11/1995 | Belleau et al. |
| 5,476,938 A | 12/1995 | Vemishetti et al. |
| 5,486,520 A | 1/1996 | Belleau et al. |
| 5,506,347 A | 4/1996 | Erion et al. |
| 5,512,596 A | 4/1996 | Kim et al. |
| 5,514,557 A | 5/1996 | Moghaddam |
| 5,514,798 A | 5/1996 | Bischofberger et al. |
| 5,519,021 A | 5/1996 | Payne et al. |
| 5,538,975 A | 7/1996 | Dionne |
| 5,587,480 A | 12/1996 | Belleau et al. |
| 5,618,820 A | 4/1997 | Dionne |
| 5,618,964 A | 4/1997 | Cheng et al. |
| 5,627,186 A | 5/1997 | Cameron et al. |
| 5,663,159 A | 9/1997 | Starrett, Jr. et al. |

(Continued)

FOREIGN PATENT DOCUMENTS

| | | |
|---|---|---|
| EP | 0 182 024 A2 | 5/1986 |
| EP | 0 206 459 A2 | 12/1986 |
| EP | 0 269 947 A1 | 6/1988 |
| EP | 0 369 409 A1 | 5/1990 |
| EP | 0 382 526 A2 | 8/1990 |

(Continued)

OTHER PUBLICATIONS

"AIDS," Monthly Index of Medical Specialties, pp. 194-198 (2002).
"Anti-HIV Drug Updates—Three Drugs on the Near Horizon," Project Inform Perspective 35:4-7 (2003).
"Atripla Fact Sheet", www.fda.gov, [Online], Jul. 12, 2006, pp. 1-2 retrieved from the internet www.fda.gov/cder/drug/inforpage/atripla/factsheet.htm [retrieved on Jan. 31, 2007.

(Continued)

*Primary Examiner* — Walter Webb
(74) *Attorney, Agent, or Firm* — Gilead Sciences, Inc.

(57) ABSTRACT

This invention is directed to a composition comprising dry granulated tenofovir DF and emtricitabine, and a method for making same. Dry granulation was unexpectedly found to be important in preparing a tenofovir DF containing composition suitable for inclusion in a combination dosage form containing emtricitabine, efavirenz and tenofovir DF.

9 Claims, No Drawings

(56) References Cited

U.S. PATENT DOCUMENTS

| | | | |
|---|---|---|---|
| 5,696,254 A | 12/1997 | Mansour et al. |
| 5,733,788 A | 3/1998 | Bischofberger |
| 5,744,596 A | 4/1998 | Mansour et al. |
| 5,756,706 A | 5/1998 | Mansour et al. |
| 5,763,606 A | 6/1998 | Mansour et al. |
| 5,792,756 A | 8/1998 | Starrett, Jr. et al. |
| 5,798,340 A | 8/1998 | Bischofberger et al. |
| 5,814,639 A | 9/1998 | Liotta et al. |
| 5,859,021 A | 1/1999 | Cameron et al. |
| 5,905,082 A | 5/1999 | Roberts et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,057,305 A | 5/2000 | Holy et al. |
| 6,069,249 A | 5/2000 | Arimilli et al. |
| 6,069,252 A | 5/2000 | Liotta et al. |
| 6,113,920 A | 9/2000 | Maye et al. |
| 6,114,343 A | 9/2000 | Liotta et al. |
| 6,121,315 A | 9/2000 | Nair et al. |
| 6,180,639 B1 | 1/2001 | Coates et al. |
| 6,194,391 B1 | 2/2001 | Schinazi et al. |
| 6,312,662 B1 | 11/2001 | Erion et al. |
| 6,639,071 B2 | 10/2003 | Thompson et al. |
| RE38,333 E | 11/2003 | Arimilli et al. |
| 6,642,245 B1 | 11/2003 | Liotta et al. |
| 6,703,396 B1 | 3/2004 | Liotta et al. |
| 6,812,233 B1 | 11/2004 | Liotta |
| 6,939,964 B2 | 9/2005 | Thompson et al. |
| 7,094,413 B2 | 8/2006 | Buelow et al. |
| 7,795,217 B2 | 9/2010 | Adra |
| 7,851,165 B2 | 12/2010 | Fuhrmann et al. |
| 8,067,473 B2 | 11/2011 | Alchanati et al. |
| 2001/0012518 A1 | 8/2001 | Makool-Moorehead et al. |
| 2001/0014352 A1 | 8/2001 | Batra et al. |
| 2003/0203969 A1 | 10/2003 | Bevec et al. |
| 2004/0180089 A1 | 9/2004 | Plachetka et al. |
| 2004/0224917 A1 | 11/2004 | Dahl et al. |
| 2004/0253218 A1 | 12/2004 | Eisenbach-Schwartz et al. |
| 2005/0197320 A1 | 9/2005 | Chen et al. |
| 2006/0128692 A1 | 6/2006 | Chen et al. |
| 2006/0246130 A1 | 11/2006 | Dahl et al. |
| 2007/0036861 A1 | 2/2007 | Oury et al. |
| 2007/0077295 A1 | 4/2007 | Dahl et al. |
| 2007/0099902 A1 | 5/2007 | Dahl et al. |
| 2009/0036408 A1 | 2/2009 | Dahl et al. |
| 2009/0143314 A1 | 6/2009 | Dahl et al. |

FOREIGN PATENT DOCUMENTS

| | | |
|---|---|---|
| EP | 0 481 214 A1 | 4/1992 |
| EP | 0 482 657 A2 | 4/1992 |
| EP | 0 632 048 A1 | 1/1995 |
| EP | 0 647 649 A1 | 4/1995 |
| EP | 0 694 547 A2 | 1/1996 |
| EP | 1 256 585 A1 | 11/2002 |
| EP | 1 332 757 A1 | 8/2003 |
| GB | 942 152 A | 11/1963 |
| GB | 1 523 865 A | 9/1978 |
| GB | 2 111 043 A | 6/1983 |
| WO | WO 88/05438 | 7/1988 |
| WO | WO 91/19721 A1 | 12/1991 |
| WO | WO 92/01698 | 2/1992 |
| WO | WO 92/09611 A1 | 6/1992 |
| WO | WO 92/13869 | 8/1992 |
| WO | WO 92/14743 A2 | 9/1992 |
| WO | WO 93/03027 A1 | 2/1993 |
| WO | WO 94/03466 | 2/1994 |
| WO | WO 94/03467 A2 | 2/1994 |
| WO | WO 95/07919 | 3/1995 |
| WO | WO 95/07920 A1 | 3/1995 |
| WO | WO 95/32957 A1 | 12/1995 |
| WO | WO 96/18605 A1 | 6/1996 |
| WO | WO 98/04569 A1 | 2/1998 |
| WO | WO 99/25352 A1 | 5/1999 |
| WO | WO 99/61026 | 12/1999 |
| WO | WO 00/25797 A1 | 5/2000 |
| WO | WO 01/64221 A1 | 9/2001 |
| WO | WO 02/08241 A2 | 1/2002 |
| WO | WO 02/062123 A2 | 8/2002 |
| WO | WO 02/068058 A2 | 9/2002 |
| WO | WO 02/070518 A1 | 9/2002 |
| WO | WO 03/045327 A2 | 6/2003 |
| WO | WO 03/059327 | 7/2003 |
| WO | WO 2004/052296 A2 | 6/2004 |
| WO | WO 2004/064845 A1 | 8/2004 |
| WO | WO 2005/021001 A1 | 3/2005 |
| WO | WO 2006/135933 A2 | 12/2006 |
| WO | WO 2006/135993 A1 | 12/2006 |
| WO | WO 2007/068934 A2 | 6/2007 |

OTHER PUBLICATIONS

"Gilead Buys Triangle in $464M Deal" Pharma Marketletter, 1 page (Dec. 9, 2002).

"Gilead Captures Triangle for $464 Million," Chemical Market Reporter 262(21):1 page (Dec. 9, 2002).

"Gilead set to acquire Triangle for $464m," BT Catalyst 17(1):1 page (Jan. 1, 2003).

"HIV Treatment Information," Project Inform, (on line), Jan. 2006, pp. 1-3, retrieved from http://www.projinf.org/bn/news_013006.html [retrieved on Jan. 31, 2007].

"Pill" Encarta Dictionary, 2 pages. (2009).

"Rescriptor," Patient Prescribing Information Leaflet, 7 pages. (2001).

"Scientific Discussion," EMEA, pp. 1/28-3/28, European Medicines Agency: (Feb. 2005).

"Time-Release," Compact Oxford English Dictionary, 1 page (2009).

Adis Data Information, "Emtricitabine/Tenofovir Disoproxil Fumarate," Drugs in R & D 5(3):160-161 (2004).

Alexander et al., "Investigation of (Oxodioxolenyl)methyl carbamates as nonchiral bioreversible prodrug moieties for chiral amines," J. Med. Chem. 39:480-486, 1996.

Amended Answer and Counterclaim against Gilead Sciences, Inc. filed by Teva Pharmaceuticals USA, Inc and Teva Pharmaceuticals Industries, Ltd. Case No. 08-CV-10838 (Jul. 20, 2009).

Anderson, "Antiviral dynamics and sex differences of zidovudine and lamivudine triphosphate concentrations in HIV-infected individuals," AIDS 17:2159-2168 (2003).

Ansel et al., "Pharmaceutical Dosage Forms and Rug Delivery Systems," 7th Edition, Lippincott Williams & Wilkins, pp. 209-213 (1999).

Answer and Counterclaim against Gilead Sciences, Inc. filed by Teva Pharmaceuticals USA, Inc and Teva Pharmaceuticals Industries, Ltd. Case No. 08-CV-10838 (Feb. 5, 2009).

Answer filed by Teva Pharmaceuticals USA, Inc and Teva Pharmaceuticals Industries, Ltd. Case No. 10-CV-01796 (May 10, 2010).

Answer filed by Teva Pharmaceuticals USA, Inc and Teva Pharmaceuticals Industries, Ltd. Case No. 10-CV-01851 (May 17, 2010).

Arimilli et al., "Orally bioavailable acylic nucleoside phosphonate prodrugs: Adefovir, Dipivoxil and Bis(POC)PMPA," vol. 3 (accepted for publication), Adv. Antiviral Drug Design, 1998.

Arimilli et al., "Synthesis, in vitro biological evaluation and oral bioavailability of 9-[2-(phosphonomethoxy)propyl]adenine (PMPA) prodrugs," Antiviral Chem. & Chemo. 8(6):557-567, 1997.

Arribas et al., "Tenofovir Disoproxil Fumarate, Entricitabine and Efavirenz Compared with Zidovudine/Lamivudine and Efavirenz in Treatment-Naive Patients 144-Week Analysis," JAIDS 47(1):74-78 (2008).

Balzarini et al, "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine." Antimicrob Agents Chemother. Feb. 1993; 37(2): 332-338.

Banker, Modern Pharmaceutics, Drugs and the Pharmaceutical Sciences, p. 340, Mercel Dekker, Inc. 1996.

(56) References Cited

OTHER PUBLICATIONS

Bartlett et al., "Overview of the effectiveness of triple combination therapy in antiretroviral-naive HIV-1 infected adults," AIDS 15:1369-1377 (2001).
Beauchamp et al., "Amino acid ester prodrugs of acyclovir," Antivir. Chem. and Chemoth. 3(3):157-64, 1992.
Benzaria et al., "New prodrugs of 9-(2-phosphonomethoxyethyl)adenine (PMEA): Synthesis and stability studies," Nucls. & Nuclt. 14(3-5):563-565, 1995.
Benzaria et al., "Synthesis, in Vitro Antiviral Evaluation, and Stability Studies of Bis(S-acyl-2-thioethyl) Ester Derivatives of 9-[2-(Phosphonometyoxy)ethyl]adenine (PMEA) as Potential PMEA Prodrugs with Improved Oral Bioavailability," J. Med. Chem. 39:4958-4965 (1996).
Berge et al., "Pharmaceutical salts," J. Pharm. Sci. 66(1):1-19, 1977.
Blackburn et al., "DNA and RNA structure," pp. 15-81, Nucleic Acids in Chemistry and Biology, 1996.
Bristol Myers Squibb "Sustiva®," http://www.fda.gov/medwaTCH/SAFETY/2005/Sustiva_PI61005.pdf, pp. 3-40 (retrieved Jan. 31, 2007).
Bundgaard et al., "Design and Application of Prodrugs," pp. 113-191, Textbook of Drug Design and Development, 1991.
Byrn (editor), Solid State Chemistry of Drugs, 2cd Edition, p. 22, 1999.
Colla et al., "Synthesis and antiviral activity of water-soluble esters of acyclovir [9-[(2-Hydroxyethoxy)methyl]guanine]," J. Med. Chem. 26:602-04, 1983.
Communication about intention to grant a European patent for Patent Publication EP 1583542 (Application No. 04701819.7) issued by the European Patent Office (Nov. 5, 2007).
Communication and Annex for Patent Publication EP 1583542 (Application No. 04701819.7) issued by the European Patent Office (Jul. 17, 2007).
Communication and Annex for Patent Publication EP 1583542 (Application No. 04701819.7) issued by the European Patent Office (Jul. 26, 2006).
Communication and Annex for Patent Publication EP 1583542 (Application No. 04701819.7) issued by the European Patent Office (Oct. 24, 2005).
Communication from the Examining Division of the EPO for EP 1890681 B1 (Application No. 06773194.3) (May 13, 2009).
Communication of further notices of opposition pursuant to Rule 79(2) EPC for EP 1583542 B1 (Application No. 04701819.7) and Request to File Observations (Apr. 23, 2009).
Communication of Intent to Grant EP 1890681 B1 (Application No. 06773194.3) and Druckexemplar issued by the European Patent Office (Jul. 15, 2008).
Communication of notices of opposition pursuant to Rule 79(2) EPC for EP 1890681 B1 (Application No. 06773194.3) and Request to File Observations (Nov. 12, 2009).
Communication pursuant to Article 94(3) EPC for Patent Publication EP 1923063 (Application No. 08152527.1) issued by the Europea n Patent Office (Sep. 4, 2009).
Complaint for Patent Infringement against Teva Pharmaceuticals USA, Inc and Teva Pharmaceuticals Industries, Ltd. filed by Gilead Sciences, Inc. and Emory University Case No. 10-CV-01798 (Mar. 5, 2010).
Complaint for Patent Infringement against Teva Pharmaceuticals USA, Inc and Teva Pharmaceuticals Industries, Ltd. filed by Gilead Sciences, Inc. Case No. 08-CN-10838 (Dec. 12, 2008).
Complaint for Patent Infringement against Teva Pharmaceuticals USA, Inc and Teva Pharmaceuticals Industries, Ltd. filed by Gilead Sciences, Inc. Case No. 10-CV-01796 (Mar. 5, 2010).
Complaint for Patent Infringement against Teva Pharmaceuticals USA, Inc and Teva Pharmaceuticals Industries, Ltd. filed by Merck, Sharp & Dohme Corp and Bristol-Myers Squib Company. Case No. 10-CV-01851 (Mar. 9, 2010).
Conference Call Transcript—Gilead Sciences Conference call to Discuss Triangle Pharmaceuticals Acquisition. Event Date/Time Dec. 4, 2002/ 9:00 AM ET (11 pages).
Correction of an Error in the Decision According to Rule 140 EPC for EP 1890681 B1 (Application No. 06773194.3) (Jul. 5, 2011).
Dando et al., "Emtricitabine/Tenofovir Disoproxil Fumarite," Drugs 64(18):2075-2082 (2004).
Davidsen et al., "N-(Acyloxyalkyl)pyridinium salts as soluble prodrugs of a potent platelet activating factor antagonist," J. Med. Chem. 37(26):4423-4429, 1994.
De Clercq et al., "(S)-9-(2,3-dihydroxypropyl)adenine: An aliphatic nucleoside analog with broad spectrum antiviral activity," Science 200:563-565, 1978.
De Clercq, "Antiviral drugs: current state of the art," J. Clin. Virol. 22:73-89 (2001).
De Clercq et al., "New Developments in Anti-HIV Chemotherapy," Curr. Med. Chem. 8(13):1543-1572 (2001).
De Clercq et al., "New developments in ainti-HIV chemotherapy," Farmaco 56(1-2):3-12 (2001).
De Clercq, "Highlights in the Development of New Antiviral Agents," Mini-Rev. Med. Chem. 2(2):163-175 (2002).
De Clercq, "New developments in anti-HIV chemotherapy," Biochem Biophys Acta 1587(2-3):158-175 (2002).
De Lombaert et al., "N-Phosphonomethyl Dipeptides and their Phosphonate Prodrugs, a New Generation of Neutral Endopeptidase (NEP, EC 3.4.24.11) Inhibitor," J. Med. Chem. 37:498-511 (1994).
Decision of Hearing of the Indian Patent Office for Patent Application No. 3383/DELNP/2005 (Mar. 25, 2009).
Decision of Rejection for Application No. 7000806/1999 issued by the Korean Intellectual Property Office (Jan. 20, 2006) (translation).
Decision of Rejection for Patent Application No. 7000636/2000 issued by the Korean Intellectual Property Office (May 10, 2006) (translation).
Decision of Rejection for Patent Application No. 7007002/2008 issued by the Korean Intellectual Property Office (Jan. 7, 2009) (translation).
Decision of Rejection for Patent Application No. 86110757 issued by the Intellectual Property Office of Taiwan (Nov. 11, 1999) (translation).
Decision of Rejection for Patent Application No. 87112168 issued by the Taiwanese Intellectual Property Office (Apr. 6, 2001) (translation).
Decision of the Opposition Division for EP Patent EP 1583542 B1 (Application No. 04701819.7), Claims, Grounds for the Decision and Provision of the minutes (Jan. 31 and Feb. 14, 2011).
Decision to Grant Patent Application No. 06773194.3 (EP 1890681B1 ) issued by the European Patent Office (Dec. 11, 2008).
Declaration of Colleen Tracy in Support of a Motion for Leave to File Amended Complaint Case No. 10-CV-01796 (Apr. 11, 2011).
Declaration of James Galbraith in Opposition of a Motion for Leave to File Amended Complaint Case No. 10-CV-01796 (Apr. 25, 2011).
Delehanty et al. Slides from the oral presentation for "A Randomized Study of Three Doses of FTC Versus 3TC in HIV-Infected Patients," 6th CROI (Jan. 3-Feb. 4, 1999) Chicago.
Delehanty et al., "A Phase I/II Randomized, Controlled Study of FTC Versus 3TC in HIV-Infected Patients," 6th CROI (Jan. 31-Feb. 4, 1999) Chicago, Session 5, Abstract 16.
Drugs and the Pharmaceutical Sciences, vol. 1999, p. 60 (Mark Gibson, ed), 2009.
Engel, R., "Phosphonates as analogues of natural phosphates," Chem. Rev. 77(3):349-367, 1977.
Examination Report for Patent Application No. 540728 issued by the Intellectual Property Office of New Zealand (Apr. 24, 2007).
Examination Report Patent Application No. 564045 issued by the Intellectual Property Office of New Zealand (Oct. 6, 2009).
Examiner's First Report on Patent Application No. 2009200414 issued by the Australian Patent Office (Feb. 24, 2010).
Examiner's First Report on Patent Application No. 85827/98 issued by the Australian Patent Office (Feb. 28, 2001).
Examiner's First Report Patent Application No. 20026257795 issued by the Australian Patent Office (Sep. 29, 2009).
Examiner's Remarks for Patent Application No. a 2008 00493 issued by the Ukrainian Patent Office (2010).
Examiner's Second Report on Patent Application No. 85827/98 issued by the Australian Patent Office (Mar. 27, 2002).

(56) References Cited

OTHER PUBLICATIONS

Examiner's First Report on Patent Application No. 2004206821 issued by the Australian Patent office (Aug. 28, 2007).
Examiner's Remarks for Patent Application No. 200501134/28 issued by the Eurasian Patent Office (received Jul. 30, 2009) (translation).
Examiner's Second Report on Patent Application No. 2004206821 issued by the Australian Patent office (Aug. 20, 2008).
Extended European Search Report for Patent Publication EP 1923063 (Application No. 08152527.1) issued by the European Patent Office (Mar. 10, 2009).
Farquhar et al., "Biologically Reversible Phosphate-Protective Groups," J. Pharm. Sci. 72:324-325 (1983).
Farquhar et al., "Synthesis and antitumor evaluation of Bis[(pivaloxy)methyl] 2'-deoxy-5-fluorouridine 5'-monophosphate (FdUMP): a strategy to introduce nucleotides into cells," J. Med. Chem. 37(23):3902-03, 1994.
Fasman et al., pp. 385-394, Practical Handbook of Biochem. and Molec. Biol., 1989.
FDA: "Guidance for industry fixed dose combination and co-packaged drug products for treatment of HIV," www.fda.org. [on line], May 2004, pp. 1-17, (retrieved from http://www.fda.gov/oc/initiatives/hiv/hivguidance.html>[retrieved on Jan. 31, 2007].
Fell et al., "The tensile strength of lactose tablets" J. Pharm. Pharmacol. 20:657-659 (1968).
Feng et al. 2009 "The triple combination of tenofovir, emtricitabine and efavirenz show synergistic anti-HIV-1 activity in vitro: a mechanism of action study," Retrovirology 6:44, http://www.retrovirology.com/content/6/1/44.
Feng, J. et al, "Mechanistic studies show that 9-)-FTC-TP is a better inhibitor of HIV-1 reverse transcriptase than 3TC-TP," FASEB 13:1511-1517 (1999).
Final Office Action for Patent Application No. 86110757 issued by the Intellectual Property Office of Taiwan (Sep. 5, 2000) (translation).
Final Office Action for Patent Application. No. 89123708 issued by the Intellectual Property Office of Taiwan (Apr. 12, 2001) (translation).
First Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Jul. 1, 2009).
First Examination Report for Application No. 564102 Issued by the Intellectual Property Office of New Zealand (Oct. 6, 2009).
First Examination Report for Patent Application No. 3383/DELNP/2005 from the Indian Patent Office (Jul. 31, 2007).
First Examination Report for Patent Application No. 602/DEL/2007 issued by the Indian Patent Office (Nov. 18, 2009).
First Office Action for Patent Application No. 200410046290.X issued by the Chinese Patent Office (Jun. 17, 2005) (translation).
First Office Action for Patent Application No. 200480002190.5 issued by the Patent Office of the People's Republic of China (Aug. 4, 2006).
First Office Action for Patent Application No. 200510099916.8 issued by the Chinese Patent Office (Jun. 15, 2007) (translation).
First Office Action for Patent Application No. 97197460.8 issued by the Chinese Patent Office (Jan. 16, 2004) (translation).
First Official Action for Patent Application No. a 2008 00555 issued by the Ukrainian Patent Office (2011) (translation).
Fiske et al., "Pharmacokinetics, safety and tolerability of single escalating doses of DMP 266, an HIV non-nucleoside reverse transcriptase inhibitor, in healthy volunteers," Pharm. Res. 14(11 Suppl.):S609 (1997).
Flaherty et al., "Synthesis and selective monoamine oxidase B-inhibiting properties of 1-Methyl-1,2,3,6-tetrahydropyrid-4-yl carbamate derivatives: potential prodrugs of (R)- and (S)-Nordeprenyl," J. Med. Chem. 39:4759-4761, 1996.
Folkmann et al., "Acyloxymethyl carbonochloridates. New intermediates in prodrug synthesis," Synthesis, pp. 1159-1166, 1990.
Frampton et al., "Emtricitabine: A Review of Its Use in the Management of HIV Inspection," Drugs 65(10):1427-1448 (2005).
Freeman et al.., "3 Prodrug Design for Phosphate and Phosphonates," Progress in Medicinal Chemistry 34:112-147 (1997).
Fridland, "Tenofovir," Curr. Opin. Anti-Infect. Invest. Drugs 2(3):295-301 (2000).
Fung et al., "Tenofovir Disoproxil Fumarate: A Nucleotide Reverse Transcriptase Inhibitor for the Treatment of HIV Infection," Clin. Therapeutics 24(10):1515-1548 (2002).
Further Examination Report for Patent Application No. 540728 issued by the Intellectual Property Office of New Zealand (Feb. 11, 2008).
Further Examination Report for Patent Application No. 540728 issued by the Intellectual Property Office of New Zealand (Jun. 18, 2008).
Generics [UK] Limited, Notice of Opposition of EP Patent EP 1583542B1 (Application No. 04701819.7) (Mar. 18, 2009).
Generics [UK] Limited, Written Submission in preparation for Oral Proceedings for EP Patent EP 1583542 B1 (Application No. 04701819.7) (Sep. 17, 2010).
Gilead "Truvada®," http://www.fda.gov/medwatch/SAFETY/2005/Oct_PI/Truvada_PI.pdf, pp. 1-29 (retrieved Jan. 31, 2007).
Gilead Sciences Inc., Appeal Grounds against the Decision of the Opposition Division for EP 1890681 B1 (Application No. 06773194.3) (Oct. 17, 2011).
Gilead Sciences Inc., Notice of Appeal against the Decision of the Opposition Division for EP 1890681 B1 (Application No. 06773194.3) (Aug. 16, 2011).
Gilead Sciences Inc., Written Submission in preparation for Oral Proceedings for the Opposition of EP 1890681 B1 (Application No. 06773194.3) (Feb. 4, 2011).
Gilead Sciences Inc., Written Submission in preparation for Oral Proceedings for the Opposition of EP 1890681 B1 (Application No. 06773194.3) (Mar. 2 & 4, 2011).
Gilead Sciences Inc., Written Submission in preparation to/during Oral Proceedings for EP Patent EP 1583542 B1 (Application No. 04701819.7) (Sep. 17, 2010).
Gilead Sciences, Inc., "Data Comparing Viread (R) and Emtriva (R) to Combivir (R) as Part of Combination HIV Therapy Published in New England Journal of Medicine," p. 1-5, Press Release, 2006.
Gilead Sciences, Inc., "Gilead Sciences to Acquire Triangle Pharmaceuticals for $464 Million; Gilead to Launch Coviracil in 2003; Will Develop Co-Formulation of Viread and Coviracil," 2 pages, Press Release (2002).
Gilead Sciences, Inc., "U.S. FDA Approves Gilead Sciences' Emtriva A one-capsule, Once-Daily Medication for the Treatment of HIV," pp. 3-7, Press Release, 2003.
Gilead Sciences, Inc., Physician Insert for Truvada, pp. 1-30 (2007).
Gilead, Bristol-Myers Squibb "Atripla™," http://www.fda.gov/cder/foi/;abe;/2006/0219371b1.pdf, pp. 4-53 (retrieved Jan. 31, 2007).
Gilead: "Bristol-Myers Squibb and Gilead announce data supporting bioequivalence for single PIII fixed dose regimen of Sustiva® (efavirenz) and Truvada® (emtricitabine and tenofovir fumarate)" Gilead Press Release (online Jan. 9, 2006), pp. 1-5, retrieved from http://www.gilead.com/press.
Gilead: "Gilead provides update on development of fixed-dose regimen of Truvada (emtricitabine and tenofovir disoproxil fumarate) and Sustiva (efavirenz)," Gilead Press Release, [on line], Apr. 26, 2005, pp. 1-3, retrieved from http://www.gilead.com/press.
Hammer et al., "Ether, carbonate and urethane deoxynucleoside derivatives as prodrugs," Acta Chemica Scandinavia 50:609-622, 1996.
Harris et al., "Genotypic Analysis of HIV-1 Infected ART Naive Patients Receiving Emtricitabine (FTC) or Lamivudine (3TC) in a Double Blind Equivalence Trial," 5th International Workshop on Drug Resistance and Treatment Strategies, Jun. 4-8, No. 104 (2001).
Havlir et al., "In Vivo Antagonism with Zidovudine plus Stavudine Combination Therapy," J. Infect. Disease 182:321-325 (2000).
Hazen et al., "Relative Anti-HIV-1 Efficacy of Lamivudine and Emtricitabine In Vitro Is Dependent on Cell Type," J. AIDS 32:255-258 (2003).

(56) References Cited

OTHER PUBLICATIONS

Hostetler et al., "Greatly Enhanced Inhibition of Human Immunodeficiency Virus Type 1 Replication in CEM and HT 4-6C Cells by 3'-Deoxythymidine Diphosphate Dimyristoylglycerol, a Lipid Prodrug of 3'-Deoxythymidine," Antimicro. Agent Chemo. 36(9):2025-2029 (1992).
Hostetler et al.., "Synthesis and Antiretroviral Activity of Phospholipid Analogs of Azidothymidine and Other Antiviral Nucleosides," J. Biol. Chem. 265(11):6112-6117 (1990).
Ibbotson et al., Drugs 2003, 63(11), 1089-1096.
Ikeda et al., "Studies of prodrugs III. A convenient and practical preparation of Amphicillin prodrugs," Chem. Pharm. Bull. 32:4316-4322, 1984.
Information about the Results of Oral Proceedings for EP Patent EP 1583542 B1 (Application No. 04701819.7), Claims, Amended Claims and Minutes of the Oral Proceeding (Nov. 19, 2010).
International Preliminary Report on Patentability for PCT/US2004/000832 (Dec. 29, 2004).
International Preliminary Report on Patentability for PCT/US2006/023222 (Oct. 8, 2007).
International Preliminary Report on Patentability for PCT/US2006/023223 (Oct. 8, 2007).
International Search Report and Written Opinion mailed Jul. 12, 2004 for PCT/US2004/000832, Int'l. Filing Date Jan. 13, 2004.
International Search Report for PCT/US1997/013244 (Oct. 20, 1997).
International Search Report for PCT/US1998/015254 (Nov. 25, 1998).
International Search Report for PCT/US2006/023222 (Feb. 23, 2007).
International Search Report for PCT/US2006/023223 (Feb. 23, 2007).
Ishida and Asao, "Self-association and unique DNA binding properties of the anti-cancer agent TAS-103, a dual inhibitor of topoisomerases I and II," Biochem. Biophys. Acta 1587(2-3):155-163 (2002).
Iyer et al., "Synthesis of acyloxyalkyl acylphosphonates as potential prodrugs of the antiviral Trisodium phosphonoformate (Foscarnet sodium)," Tet. Lett. 30(51): 7141-7144, 1989.
Jones et al.., "Minireview: nucleotide prodrugs," Antiviral Res. 27:1-17 (1995).
Kearney et al., "Effect of Demographic Variables on the Pharmacokinetics of Tenofovir DF in HIV-Infected Patients and Healthy Subjects," 41st ICAAC Abstracts, Chicago, IL, Sep. 22-25, 2001, Abstract A-504.
Khamnei et al., "Neighboring Group Catalysis in the Design of Nucleotide Prodrugs," J. Med. Chem. 39:4109-4115 (1996).
King et al. "Potency of Nonnucleoside Reverse Transcriptase Inhibitors (NNRTIs) Used in Combination with Other Human Immunodeficiency Virus NNRTIs, NRTIs, or Protease Inhibitors," Antimicrobial and Aqents and Chemotherapy 46(6):1640-1646 (2002).
Kleinebudde et al. European journal of Pharmaceutics and Biopharmaceutics, 2004, 58, 317-326.
Krise et al., "Prodrugs of phosphates, phosphonates, and phosphinates," Advanced Drug Delivery Reviews 19:287-310, 1996.
Kucera et al., "Novel Membrane-Interactive Ether Lipid Analogs That Inhibit Infectious HIV-1 Production and Induce Defective Virus Formation," AIDS Res. & Hum. Retro. 6:491-501 (1990).
Lachman, et al. (1987) "The Theory and Practice of Industrial Pharmacy", Varghese Publishing House, Dadar Bombay, pp. 330-331.
Landgrebe, J. A., "Crystallization and filtration," Theory and Practice in the Organic Laboratory, 3rd Edition, pp. 65-77, 1982.
Letter Regarding the Opposition Procedure for EP Patent EP 1583542 B1 (Application No. 04701819.7) (Mar. 11, 2010).
Lieberman et al., "," Pharmaceutical Dosage Forms 1:177-178 (1989).
Lindahl et al., "Synthesis of an acyloxymethyl prodrug of the Inositol phosphate alpha-Trinositol," J. Carbohydrate Chemistry 15(5):549-554, 1996.
Liu et al., "Thymidylate synthase as a translational regulator of cellular gene expression," Biochem. Biophys. Acta 1587(2-3):174-182 (2002).
Loveday, "Nucleoside reverse transcriptase inhibitor resistance," JAIDS 26:S10-S24 (2001).
Maillard et al., "Adenosine receptor prodrugs: Synthesis and biological activity of derivatives of potent A1-selective agonists," J. Pharm. Sci. 83(1):46-53, 1994.
Margot et al., "Development of HIV-1 Drug Resistance Through 144 Weeks in Antiretroviral-Naive Subjects on Emtricitabine, Tenofovir Disoproxil Fumarate, and Efavirenz Compared with Lamivudine/Zidovudine and Efavirenz in Study GS-01-934," JAIDS 52(2):209-221 (2009).
Margot et al., "Genotypic and phenotypic analyses of HIV-1 in antiretroviral-experienced patients treated with tenofovir DF," AIDS 16:1227-1235 (2002).
Margot et al., "Resistance development over 144 weeks in treatment-naive patients receiving tenofovir disoproxil fumarate or stavudine with lamivudine and efavirenz in Study 903," HIV Medicine 7:442-450 (2006).
Masho et al., "Review of Tenofovir-Emtricitabine," Ther. Clin. Risk Manag. 3(6):1097-1104 (2007).
McColl et al., "Pooled Analysis of Recent Emtricitabine and Lamivudine Clinical Trials Reveals Differences in Rates of Development of the M184V/I Mutation," Poster No. PE7.3/17, 10th European AIDS Conference (EACS) Nov. 17-20, 2005, Dublin Ireland.
McIntee et al., "Probing the mechanism of action and decomposition of amino acid phosphomonoester amidates of antiviral nucleoside prodrugs," J. Med. Chem. 40(2):3323-31, 1997.
Memorandum of Law in Opposition of a Motion for Leave to File Amended Complaint Case No. 10-CV-01796 (Apr. 25, 2011).
Miller et al., Sixth International Congress on Drug Therapy in HIV Infection, Nov. 17-21, 2002 (1 page).
Mills et al., "ARTEMIS: Efficacy and Safety of Darunavir/ritonavir (DRV/r) 800/100mg Once-daily vs Lopinavir/ritonavir (LPV/r) in Treatment-naive, HIV-1-infected Patients at 96 wks," 48th Annual ICAAC/IDSA, 46th Annual Meeting, Washington, D.C. Oct. 25-28, 2008, Presentation No. H-1250c.
Minutes of the Oral Proceedings before the Opposition Division for EP 1890681 B1 (Application No. 06773194.3) and Appendices (Apr. 5, 2011).
Molina et al., "A Lopinavir/Ritonavir-Based Once-Daily Regimen Results in Better Compliance and Is Non-inferior to a Twice-Daily Regimen Through 96 Weeks," AIDS Research and Human Retroviruses 23(12):1505-1514 (2007).
Molina et al., "Once-Daily Combination Therapy with Emtricitabine, Didanosine, and Efavirenz in Human Immunodeficiency Virus-Infected Patients," J. Infect. Dis. 182:599-602 (2000).
Mulato et al., "Anti-HIV activity of adefovir (PMEA) and PMPA in combination with antiretroviral compounds: in vitro analyses," Antiviral Res. 36(2):91-97 (1997).
Murry et al., "Reversion of the M184V Mutation in Simian Immunodeficiency Virus Reverse Transcriptase is Selected by Tenofovir, Even in the Presence of Lamivudine," J. Virol. 77(2):1120-1130 (2003).
Naesens et al., "Antiretroviral activity and pharmacokinetics in mice of oral Bis(Pivaloyloxymethyl)-9-(2-phosphonylmethoxyethyl)adenine, the Bis(Pivaloyloxymethyl)ester prodrug of 9-(2-Phosphonylmethoxyethyl)adenine," Antimicro AG & Chemo. 40(1)22-28, 1996.
Newman and Byrn, "Solid-state analysis of the active pharmaceutical ingredient in drug products" Drug Discovery Today, 8(19) 898-905 (2003).
Notari, "Prodrug Design," Pharmaceutical Therapy, 14:25-53, 1981.
Notice of Appeal of the Decision of the Opposition Division for EP Patent EP 1583542 B1 (Application No. 04701819.7) (Mar. 29, 2011).
Office Action for Korean Patent Application No. 7013069/2005 issued by the Korean Intellectual Property Office (May 22, 2007).
Office Action for Patent Application No. 10-2000-7000636 issued by the Korean Intellectual Property Office (Aug. 19, 2005) (translation).
Office Action for U.S. Appl. No. 08/900,752 issued by the United States Patent and Trademark Office (Apr. 16, 1998).

(56) References Cited

OTHER PUBLICATIONS

Office Action for Patent Application No. 11-510067 issued by the Japanese Patent Office (Dec. 11, 2007) (translation).
Office Action for Patent Application No. 2,261,619 issued by the Canadian Patent Office (Dec. 22, 2004).
Office Action for Patent Application No. 2,298,059 issued by the Canadian Intellectual Property Office (Apr. 25, 2007).
Office Action for Patent Application No. 2,512,475 issued by the Canadian Patent Office (Jan. 10, 2008).
Office Action for Patent Application No. 2,611,520 issued by the Canadian Patent Office (Jun. 7, 2010).
Office Action for Patent Application No. 2006-500939 issued by the Japanese Patent Office (Mar. 25, 2010).
Office Action for Patent Application No. 2006-500939 issued by the Japanese Patent Office (Nov. 9, 2009).
Office Action for Patent Application No. 7007002/2008 issued by the Korean Intellectual Property Office (Jun. 11, 2008) (translation).
Office Action for Patent Application No. 7009376/2009 issued by the Korean Intellectual Property Office (Oct. 9, 2009) (translation).
Office Action for Patent Application No. 87112168 issued by the Taiwanese Intellectual Property Office (Mar. 1, 2004) (translation).
Office Action for Patent Application No. 87112168 issued by the Taiwanese Intellectual Property Office (May 6, 2002) (translation).
Office Action for Patent Application No. 87112168 issued by the Taiwanese Intellectual Property Office (Oct. 20, 2000) (translation).
Office Action for Patent Application No. 93112403 issued by the Taiwanese Intellectual Property Office (Apr. 27, 2005) (translation).
Official Action for Application No. 095120445 issued by the Taiwanese Intellectual Property Office (Nov. 29, 2011) (translation).
Official Action for Application No. 2008-517083 issued by the Japanese Patent Office (Aug. 2, 2011) (translation).
Official Action for Ex Parte Reexamination of U.S. Patent No. 5,922,695 (Dec. 11, 2007).
Official Action for Ex Parte Reexamination of U.S. Patent No. 5,935,946 (Jan. 16, 2008).
Official Action for Ex Parte Reexamination of U.S. Patent No. 5,977,089 (Jan. 16, 2008).
Official Action for Ex Parte Reexamination of U.S. Patent No. 6,043,230 (Dec. 11, 2007).
Official Action for Patent Application No. 10-1999-7000806 issued by the Korean Intellectual Property Office (Apr. 28, 2005) (translation).
Official Action for Patent Application No. 10-508318 issued by the Japanese Patent Office (Apr. 10, 2007) (translation).
Official Action for Patent Application No. 200501134/28 issued by the Eurasian Patent Office (Dec. 25, 2008).
Official Action for Patent Application No. 200501134/28 issued by the Eurasian Patent Office (Oct. 15, 2006).
Official Action for Patent Application No. 333687 issued by the Intellectual Property Office of New Zealand (Mar. 2, 1999).
Official Action for Patent Application No. 7001077/2008 issued by the Korean Intellectual Property Office (Sep. 13, 2010).
Official Action for Patent Application No. 93100813 issued by the Taiwanese Intellectual Property Office (Jun. 22, 2005) (translation).
Official Action for Patent Application No. 200800033/27 issued by the Eurasian Patent Office (2010) (translation).
Opinion on Patent Application No. 1-2005-00812 issued by the Vietnamese Patent Office (Jul. 27, 2008).
Opponents Comments to the Reply Statement by the Applicant relating to Patent Application No. 3383/DELNP/2005 (Aug. 14, 2008).
Order Granting Request for Ex Parte Reexamination of U.S. Patent No. 5,922,695 (Jul. 13, 2007).
Order Granting Request for Ex Parte Reexamination of U.S. Patent No. 5,935,946 (Jul. 13, 2007).
Order Granting Request for Ex Parte Reexamination of U.S. Patent No. 5,977,089 (Jul. 13, 2007).
Order Granting Request for Ex Parte Reexamination of U.S. Patent No. 6,043,230 (Jul. 13, 2007).
Osol et al., Editor, Remington's Pharmaceutical Sciences, Sixteenth Edition, pp. 1554-1557, 1980.
Pallella et al., J. Med. Chem. 338:853-860 (1998).
Parikh, Handbook of Pharmaceutical Granulation Tech., NY, Marcel Dekker Inc., 1996.
Pharmaceutical Dosage Forms and Drug Delivery Systems, 6th Ed. pp. 171-174 (1995).
Pharmaceutical Technology (2005), Big Pharma Companies Team Up to Develop Once-Daily Triple-Combination HIV Drug,vol. 29, No. 4.
Piantadosi et al., "Synthesis and Evaluation of Novel Ether Lipd Nucleoside Conjugates for Anti-HIV-1 Activity," J. Med. Chem. 34:1408-1414 (1991).
Plaintiff's Reply to Teva USA's Amended Counterclaim, filed by Gilead Sciences, Emory University, Case No. 08-CV-10838 (Aug. 10, 2009).
Plaintiff's Reply to Teva USA's Second Amended Counterclaim, filed by Gilead Sciences, Emory University,Case No. 08-CV-10838 (Oct. 15, 2009).
Plaintiff's Reply to Teva's Counterclaim, filed by Gilead Sciences, Inc., Emory University Case No. 08-CV-10838 (Feb. 25, 2009).
Pozniak et al., "Tenofovir Disoproxil Fumarate, Emtricitabine, and Efavirenz Versus Fixed-Dose Zidovudine/Lamivudine and Efavirenz in Antiretroviral-Naive Patients," JAIDS 43(5):535-540 (2006).
Pre-Grant Opposition Petition against Brazilian Patent Application PI 0406760-6 (Aug. 20, 2010).
Puech et al., "Intracellular delivery of nucleoside monophosphates through a reductase-mediated activation process," Antiviral Res. 22:155-174 (1993).
Pujari et al., "Safety and long term effectiveness of generic fixed-dose formulations of nevirpine-based HAART amongst antiretroviral-naïve HIV-infected patients in India," World Health Organization, [on line], Dec. 16, 2003, pp. 99-116; (Retrieved from: http://libdoc.who.int/publications/2003/a86263.pdf.
Rejection Decision for Patent Application No. 200480002190.5 issued by the Patent Office of the People's Republic of China (Jan. 15, 2010).
Rejection of Patent Application No. 93100813 issued by the Taiwanese Intellectual Property Office (Feb. 22, 2006) (translation).
Reply of the Patent Proprietor to the Notice of Opposition of EP 1890681 B1 (Application No. 06773194.3) (Jun. 22, 2010).
Reply of the Patent Proprietor to the Notices of Opposition of EP Patent EP 1583542 B1 (Application No. 04701819.7) (Jan. 4, 2010).
Request for Ex Parte Reexamination of U.S. Patent No. 5,922,695 (submitted Apr. 30, 2007).
Request for Ex Parte Reexamination of U.S. Patent No. 5,935,946 (submitted Apr. 30, 2007).
Request for Ex Parte Reexamination of U.S. Patent No. 5,977,089 (submitted Apr. 30, 2007).
Request for Ex Parte Reexamination of U.S. Patent No. 6,043,230 (submitted Apr. 30, 2007).
Response to the Written Opinion of the ISA for PCT/US2006/023222 (May 10, 2007).
Response to the Written Opinion of the ISA for PCT/US2006/023223 (May 10, 2007).
Revised International Search Report for PCT/US2004/000832 (Aug. 5, 2004).
Revocation of European Patent EP 1890681 B1 (Application No. 06773194.3) (Jun. 8, 2011).
Richman, "Antiretroviral activity of emtricitabine, a potent nucleoside reverse transcriptase inhibitor," Antivir. Ther. 6(2):83-88 (2001).
Richman, "HIV Chemotherapy," Nature 410:995-1001 (2001).
Ristig et al., "Tenofovir Disoproxil Fumarate Therapy for Chronic Hepatitis B in Human Immunodeficiency Virus/Hepatitis B Virus-Coinfected Individuals for Whom Interferon-α and Lamivudine Therapy Have Failed," J. Infect. Dis.186:1844-1847 (2002).
Robinson et al., "Discovery of the Hemifumarate and (alpha-L-Alanyloxy)methylester as prodrugs of an antirheumatic oxindole: Prodrugs for enolic OH group," J. Med. Chem. 39:10-18, 1996.
Rousseau et al., "Prototype trial design for rapid dose selection of antiretroviral drugs: an example using emtricitabine (Coviracil)," Journal of Antimicrobial Chemotherapy 48:507-513 (2001).

(56) References Cited

OTHER PUBLICATIONS

Safadi et al., "Phosphoryloxymethyl carbamates and carbonates—Novel water soluble prodrugs for amines and hindered alcohols," Pharm. Res. 10(9):1350-1355, 1993.

Sakamoto et al., "Studies on prodrugs II. Preparation and characterization of (5-substituted 2-oxo-1,3-dioxolen-4-yl)methyl esters of Ampicillin," Chem. Pharm. Bull. 32(6):2241-2248, 1983.

Samara et al., "Pharmacokinetic analysis of Diethylcarbonate prodrugs of Ibuprofen and Naproxen," Biopharmaceutics & Drug Disposition 16:201-210, 1995.

Sanne et al., "Genotypic Analysis of HIV-1 Infected ART-Naive Patients Receiving Emtricitabine (FTC) or Lamivudine (3TC) in a Double Blind Equivalence Trial," Poster No. 4433, presented at the XIV International AIDS Conference Jul. 7-12, 2002, Barcelona, Spain.

Sanne et al., "Two Randomized, Controlled, Equivalence Trials of Emtricitabine (FTC) to Lamivudine (3TC)," Poster 4432 presented at the XIV International AIDS Conference, Jul. 7-12, 2002, Barcelona, Spain.

Schinazi et al., "Characterization of Human Immunodeficiency Viruses Resistant to Oxathiolane-Cytosine Nucleosides," Antimicrobial Agents and Chemotherapy 374:875-881 (1993).

Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," Antimricobial Agents and Chemotherapy 36(11):2423-2431(1992).

Schinazi et al., Letter to the Editor "Assessment of the Relative Potency of Emtricitabine and Lamivudine," J. AIDS 34(2)243-245 (2003).

Search and Examination Report for Appln No. AP/P/2005/003348 issued by the African Regional Intellectual Property Organization, 5 pages (Apr. 10, 2008).

Second Amended Answer and Counterclaim against Gilead Sciences, Inc. filed by Teva Pharmaceuticals USA, Inc and Teva Pharmaceuticals Industries, Ltd. Case No. 08-CV-10838 (Filed Oct. 9, 2009).

Second Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Sep. 25, 2009).

Second Office Action for Application No. 200680026180.4 issued by the State Intellectual Property Office of the People's Republic of China (Oct. 20, 2011) (translation).

Second Office Action for Patent Application No. 200510099916.8 issued by the Chinese Patent Office (Nov. 16, 2007) (translation).

Second Office Action for Patent Application No. 97197460.8 issued by the Chinese Patent Office (Aug. 5, 2005) (translation).

Second Official Action for Patent Application No. a 2005 07947 issued by the Ukrainian Patent Office (2006) (translation).

Serafinowska et al., "Synthesis and in vivo Evaluation of prodrug of 9-{2-(Phosphonomethoxy)ethoxy} adenine," J. Med. Chem. 38:1372-1379, 1995.

Shaw et al., "Metabolism and pharmacokinetics of novel oral prodrugs of 9-[(R)-2-(phosphonomethoxy)propyl]adenine (PMPA) in dogs," Pharm. Res. 14(12):1824-1829, 1997.

Siddiqui et al., "Design and Synthesis of Lipophilic Phosphoramidate D4T-MP Prodrugs Expressing High Potency Against HIV in Cell Culture: Structural Determinants for In Vitro Activity and QSAR," J. Med. Chem. 42(20):4122-4128 (1999).

Smith et al., "Randomized, double-blind, placebo-matched, multicenter trial of abavacir/lamivudine or tenofovir/emtricitabine with lopinavir/ritonavir for inital HIV treatment," AIDS 23:1547-1556 (2009).

Srinivas et al., "Metabolism and in vitro antiretroviral activities of Bis(Pivaloyloxymethyl) prodrugs of acyclic nucleoside phosphonates," Antimicro AG & Chemo. 37(10):2247-2250, 1993.

Srivastva et al., "Bioreversible phosphate protective groups: Synthesis and stability of model acyloxymethyl phosphates," Bioorg. Chem. 12:118-129, 1984.

Starret et al., "Synthesis and in vitro evaluation of a phosphonate prodrug:bis(pivaloyloxymethyl) 9-(2-phophonylmethoxyethyl)adenine," Antiviral Res. 19:267-273, 1992.

Starret et al., "Synthesis, oral bioavailability determination, and in vitro evaluation of prodrugs of the Antiviral agent 9-[2-(phosphonomethoxy)ethyl)adenine (PMEA)," J. Med. Chem. 37:1857-1864, 1994.

Substantive Examination Report for Patent Application No. W00 2005 02145 from the Indonesian Patent Office (2010).

Sueoka et al., "Pharmacokinetics of Alkoxycarbonyloxy ester prodrugs of PMPA in dogs," Abstract, American Association of Pharmaceutical Science, Western Regional Meeting, Apr. 24-25, 1997.

Summons to Attend Oral Proceedings and Annex to the Communication for EP Patent EP1583542B1 (Application No. 04701819.7) (May 21, 2010).

Summons to Attend Oral Proceedings and Annex to the Communication for the Opposition of EP 1890681 B1 (Application No. 06773194.3) (Oct. 14, 2010).

Tamari, "A Decade in HIV Treatment: What Is the State of the Art and How Did We Arrive," Clinical Excellence for Nurse Practitioners 5(1):4-12 (2001).

Teva Pharmaceutical Industries Ltd., Notice of Opposition of EP Patent EP1583542B1 (Application No. 04701819.7) (Mar. 13, 2009).

Teva Pharmaceutical Industries Ltd., Written Submission in preparation for Oral Proceedings for EP Patent EP1583542B1 (Application No. 04701819.7) (Sep. 16, 2010).

Teva Pharmaceuticals Industries Ltd., Notice of Opposition of EP 1890681B1 (Application No. 06773194.3) (Oct. 7, 2009).

Teva Pharmaceuticals Industries Ltd., Written Submission in preparation for Oral Proceedings for the Opposition of EP 1890681B1 (Application No. 06773194.3) (Mar. 17, 2011).

Third Amended Answer filed by Teva Pharmaceuticals USA, Inc and Teva Pharmaceuticals Industries, Ltd. Case No. 08-CV-10838 (Filed Aug. 6, 2010).

Third Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Jul. 6, 2010).

Third Office Action for Patent Application No. 97197460.8 issued by the Chinese Patent Office (Jun. 9, 2006) (translation).

Third Official Action for Patent Application No. a 2005 07947 issued by the Ukrainian Patent Office (2007) (translation).

Thornber "Isosterism and Molecular Modification in Drug Design" Chem. Soc. Reviews 18: 563-580, 1979.

Tisdale et al., "Rapid in vitro selection of human immunodeficiency virus type 1 resistant to 3'-thiacytidine inhibitors due to a mutation in the YMDD region of reverse transcriptase," Proc. Natl. Acad. Sci. USA 90:5653-5656 (1993).

Tsai et al., "Effects of (R)-9-(2-phophonylmethoxypropyl)adenine monotherapy on chronic SIV infection in macaques," AIDS Res. & Hum. Retro. 13(8):707-712, 1997.

Tsai et al., "Prevention of SIV infection in macaques by (R)-9-(2-phosphonylmethoxypropyl)adenine," Science 270:1197-1199, 1995.

U.S. Department of Health and Human Services (2004) "Guidance for Industry Fixed Dose Combination and Co-Packaged Drug Products for Treatment of HIV—Draft Guidance" pp. 1-21.

Ueda et al., "Vinyl compounds of nucleic acid bases I. Synthesis of N-vinyluracil, N-vinylthymine, and N-vinyladenine," Die Makromolekulare Chemie 120:13-20, 1968.

USP 24 The United States Pharmacopeia (2000).

Wainberg et al. "In vitro selection and characterization of HIV-1 with reduced susceptibility to PMPA," Antiviral Therapy 4:87-94 (1999).

Walmsley et al., "Gemini: A Noninferiority Study of Saquinavir/Ritonavir Versus Lopinavir/Ritonavir as Initial HIV-1 Therapy in Adults," J. Acquir. Immune Defic. Syndr. 50(4):367-374 (2009).

Wang et al. "Lack of Significant Pharmacokinetic Interactions between Emtricitabine and Other Nucleoside Antivirals in Healthy Volunteers," 41st ICAAC Abstracts, Chicago, IL, Sep. 22-25, 2001, Abstract A-505.

Wang et al. "Pharmacokinetic and pharmacodynamic characteristics of emtrictabine support its once daily dosing," Int. Conf. AIDS, Jul. 7-12, 14:abstract TUPeB4546 (2002).

(56) References Cited

OTHER PUBLICATIONS

Weller et al., "Orally active Fibrinogen receptor antagonists. 2. Amidoximes as prodrugs of amidines," J. Med. Chem. 39:3139-3147, 1995.
Written Opinion issued by the ISA for PCT/US2006/023223 (Feb. 23, 2007).
"Annex I. Summary of Product Characteristics," for Epivir, 9 pages.
"Annex I. Summary of Product Characteristics," for Truvada film-coated tablets, 14 pages.
Arimilli et al., "Nucleotide Analogues," U.S. Appl. No. 60/022,708, filed Jul. 26, 1996, 40 pages.
Brogan et al., "Cost-Effectiveness of Nucleoside Revers Transcriptase Inhibitor Pairs in Efavirenz-Based Regimens for Treatment-Naïve Adults with HIV Infection in the United States," Value in Health 14:657-664 (2011).
Castello and Mattocks, "Discoloration of Tablets Containing Amines and Lactose," J. Pharm. Sci. 106-108.
Cherry, et al., "Mutations at codon 184 in simian immunodeficiency virus reverse transcriptase confer resistance to the (–) enantiomer of 2,,3'-dideoxy-3,-thiacytidine.—Antimicrob.," Agents Chemother. 41:2763-2765(1997) http://aac.asm.org/content/41/12/2763.full.pdf+html (retrieved Jan. 29, 2014).
Communication of Notice of Opposition of EP1583542 B1 (Application No. 04701819.7)—first information to the patent proprietor (Mar. 24, 2009).
Communication of Notice of Opposition of EP 1583542 B1 (Application No. 04701819.7)—first information to the patent proprietor (Mar. 26, 2009).
Communication pursuant to Article 94(3) EPC for Patent Publication EP 1923063 (Application No. 08152527.1) issued by the European Patent Office (Mar. 26, 2012).
Crowley, "Drug-Excipient Interactions," Pharm. Tech., 6 pages (2001).
Dahl et al., Amended Transmittal of U.S. Appl. No. 10/540,794, Compositions and methods for combination antiviral therapy, filed Mar. 20, 2006.
De Clercq, "New Anti-HIV Agents and Targets," Medicinal Research Reviews 22(6):531-565 (2002).
Decision to Grant a European patent for EP Appln No. 04701819.7 and Druckexemplar (May 23, 2008).
Delehanty J., et al., "Selection of FTC dose based on viral kinetics and pharmacokinetics in an accelerated clinical trial design," 12th World AIDS Conference, Geneva, Switzerland, Abstract No. 12208 (Jul. 1998) http://www.aegis.org/DisplavContent/print.aspx?SectionID=341007 (retrieved Jan. 30, 2014).
Department of Health and Human Services, "Guidelines for the Use of Antiretroviral Agents in HIV-1-Infected Adults and Adolescents," pp. 1, 33-49 (Nov. 3, 2008).
Examiner's Second Report on Patent Application No. 2009200414 issued by the Australian Patent Office (Aug. 29, 2011).
European Search Report, EP 2386294 (Application No. 11167101.2), 15 pages (Dec. 29, 2011).
Eyjolfsson, "Lisinopril-Lactose Incompatibility," Drug Devel. Indust. Pharm. 24(8):797-798 (1998).
First Examination Report for Patent Application No. 6665/DELNP/2008 issued by the Indian Patent Office (Jun. 30, 2011).
Flexner, C., "HIV-Protease Inhibitors," The New England Journal of Medicine 338(18):1281-1292 (Apr. 30, 1998).
FTC 101 Virology analysis, TPI Document No. 14022 (2002).
Gallant, et al., "Early Non-Response to Tenofovir DF (TDF)+Abacavir (ABC) and Lamivudine (3TC) in a Randomized Trial Compared to Efavirenz (EFV)+ABC and 3TC: ESS30009 Unplanned Interim Analysis," Abstr Intersci Conf Antimicrob Agents Chemother Intersci Conf Antimicrob Agents Chemother, Abstract No. H-1722a (2003).
Giron, "Applications of thermal analysis in the pharmaceutical industry," J. Pharm. Biomed. Anal. 4(6):755-770 (1986).
Glaxo Marketing Material, Epivir+Ziagen, 6 pages (2003).
Gosselin, et al., "Anti-human immunodeficiency virus activities of the (3-L enantiomer of 2',3'-dideoxycytidine and its 5-fluoro derivative in vitr," Antimicrob Agents Chemother 38: 1292-1297 (1994) http://aac.asm.org/content/38/6/1292.full.pdf (retrieved Jan. 30, 2014).
Harrigan, P.R., et al., "Phenotypic susceptibilities to tenofovir in a large panel of clinically derived human immunodeficiency virus type 1 isolates," Antimicrob Agents Chemother 46:1067-1072 (2002) http://aac.asm.Org/content/46/4/1067.full.pdf+html (retrieved Jan. 30, 2014).
Huff, "Five New Drugs Enter the Homestretch," The Body: The Complete HIV/AIDS Resource, 3 pages (2002).
Information About the Results of the Oral Proceedings for EP 1890681 B1 (Application No. 06773194.3) (Apr. 5, 2011).
Jamsek, et al. "Poor Virological Responses and Early Emergence of Resistance in Treatment Naïve, HIV-infected Patients Receiving a Once Daily Triple Nucleoside Regimen of Didanosine, Lamivudine, and Tenofovir DF" 11th Conf Retrovir Oppor Infect, Abstract No. 51 (2004).
Kusmierek et al., "Kinetics and Mechanisms of Hydrolytic Reactions of Methylated Cytidines under Acidic and Neutral Conditions," Acta Chem. Scand. 43:196-202 (1989).
Lanier, et al. "Prediction of NRTI Optins by Linking Reverse Transcriptase Genotype to Phenotypic Breakpoints" 10th Conf Retrovir Oppor Infect, Abstract No. 586 (2003.
Lindahl, "Instability and decay of the primary structure of DNA," Nature 362:709-715 (1993).
Lu, et al., "Determination of Clinical Cut-Offs for Reduced Response to Tenofovir DF therapy in Antiretroviral-Experienced Patients," Antiviral Therapy 7(1):S104, Abstract No. 125 (2002).
Marcelin et al., "Resistance profiles of emtricitabine and lamivudine in tenofovir-containing regimens," J. Antimicrob. Chemother. 67:1475-1478 (2012).
Margot et al., "In Vitro Human Immunodeficiency Virus Type 1 Resistance Selections with Combinations of Tenofovir and Emtricitabine or Abacavir and Lamivudine," Antimicrobial Agents and Chemotherapy 50(12):4087-4095 (2006).
Merck Index, 13th Edition, p. ONR-65 (2001).
Miller M.D., et al., Human Immunodeficiency Virus Type 1 Expressing the Lamivudine-Associated M184V Mutation in Reverse Transcriptase Shows Increased Susceptibility to Adefovir and Decreased Replication Capability In Vitro, The Journal of Infectious Diseases 179:92-100 (1999) http://jid.oxfordjournals.org/content/179/1/92.full.pdf (retrieved Jan. 30, 2014).
Miller, Margot N.A., et al., "Antiviral activity of tenofovir (PMPA) against nucleoside-resistant clinical HIV samples," Nucleosides Nucleotides Nucleic Acids,; 20:1025-1028 (2001).
Minutes of Oral Proceedings from EPO for Application Application No. 067731595.0 dated Nov. 25, 2013.
Molina et al., "CASTLE: Atazanavir-Ritonavir vs Lopinavir-Ritonavir in Antiretroviral-Naïve HIV-1 Infected Patients: 96 Week Efficacy & Safety," 48th Annual ICAAC/IDSA 46th Annual Meeting, Washington , D.C., Presentation No. H-1250d (Oct. 25-28, 2008).
National Institutes of Health, "Guidelines for the Use of Antiretroviral Agents in HIV-1-Infected Adults and Adolescents," 9 pages (2011/2012).
Notice of Allegation and Detailed Statement in respect of Tenofovir Disoproxil Fumarate and Emtricitabine (Truvada®) and Canadian Patent Nos. 2,261,619 and 2,298,059, 56 pages (Nov. 22, 2011).
Notice of Allegation and Detailed Statement in respect of Truvada and Canadian Patent No. 2,512,475, 37 pages (Nov. 22, 2011).
Office Action for Korean Patent Application No. 7013069/2005 issued by the Korean Intellectual Property Office (Jan. 23, 2008).
Office Action for Patent Application No. 200680026180.4 issued by the Chinese Patent Office (May 29, 2013) (translation).
Office Action, 10 pages, from U.S. Appl. No. 12/195,161 (mailed May 7, 2010).
Office Action, 10 pages, from U.S. Appl. No. 12/204,174 (mailed Oct. 1, 2009).
Office Action, 7 pages, from U.S. Appl. No. 10/540,794 (mailed Sep. 21, 2006).
Office Action, 8 pages, from U.S. Appl. No. 10/540,794 (mailed Oct. 31, 2007).
Office Action, 8 pages, from U.S. Appl. No. 12/204,174 (mailed Jun. 4, 2010).

(56) References Cited

OTHER PUBLICATIONS

Office Action, 9 pages, from U.S. Appl. No. 10/540,794 (mailed May 16, 2007).
Official Action and Preliminary Notice of Allowance from the Eurasian Patent Office for Application No. 200501134/28 (May 14, 2010).
Official Action for Application No. 2008-517083 issued by the Japanese Patent Office (Mar. 23, 2012) (translation).
Official Action for Patent Application No. 93100813 issued by the Taiwanese Intellectual Property Office (Mar. 16, 2011) (translation).
Official Action, 2 pages, from JP appl. No. 2010-175808 (mailed Nov. 6, 2012) translation attached.
Official Communication for Patent Application No. 2100/DEL/2007 issued by the Indian Patent Office (Jan. 16, 2013).
Opposition filed in Indian Patent Appl. No. 9661/DELNP/2007 by Cipla Limited (Jun. 30, 2009).
Osborne, "Gilead plans $300M notes sale to recoup some merger costs.(Gilead Sciences Inc.)," Bioworld Today, 13(239), 1 pages (Dec. 16, 2002).
Osborne, "Gilead, Triangle Plan Merger: $464 Deal Pairs HIV Drugs," Bioworld Today 13(233):1,6 (2002).
Patent Examination Report No. 1, Australia patent appl. No. 2011253996, 2 pages (Nov. 15, 2012).
Pharmaceutical Dosage Forms. Tablets. 2nd Ed., revised and expanded, Lieberman et al., eds., pp. 93 and 98 (1990).
Project Inform, "Perspective," pp. 1-28 (2003).
Quan et al., "Endogenous Reverse Transcriptase Assays Reveal Synergy between Combinations of the M184V and other Drug-Resistance-conferring Mutations in Interactions with Nucleoside Analog Triphosphates," J. Mol. Biol. 277:237-247 (1998).
Reply to the statement of appeal grounds, EP 1583542 B1 (Application No. 04701819.7), 50 pages (Oct. 18, 2011).
Request for Correction of EP Appln No. 04701819.7 (Jul. 8, 2008).
Request for Correction of EP Appln No. 04701819.7 (Jun. 27, 2008).
Response to Summons and Annex from EPO for Application No. 067731595.0 dated Sep. 25, 2013.
Response to the Noting of Loss of Rights pursuant to Rule 112(1) EPC dated Sep. 3, 2012, Patent Publication EP 2386294 (Application No. 11167101.2) (Nov. 13, 2012).
Response to the Noting of Loss of Rights pursuant to Rule 112(1)EPC dated Nov. 14, 2012, Patent Publication EP 1923063 (Application No. 08152527.1) (Jan. 24, 2013).
Response to the reply letter of Teva Pharmaceutical Industries Ltd. dated Oct. 18, 2011, EP 1583542 B1 (Application No. 04701819.7), 35 pages (Aug. 9, 2012).
Reversal of Rejection Decision for Application No. 200480002190.5 by the Patent Rexamination Board (Patent Office of the People's Republic of China) (Jun. 10, 2010).
Riaz and Ami, "Stability of Aminophylline," Pak. J. Pharm. Sci. 6(1):35-44 (1993).
Robinson B.S., et al., "BMS-232632, a Highly Potent Human Immunodeficiency Virus Protease Inhibitor That Can Be Used in Combination with Other Available Antiretroviral Agents," Antimicrobial Agents and Chemotherapy 44(8): 2093-2099 (Aug. 2000) http://www.ncbi.nlm.nih.gov/pmc/articles/PMC90019/pdf/acQ02093.pdf (retrieved Jan. 30, 2014).
Scrip, "Gilead Acquires Triangle for $464 Million," 2 pages (Dec. 6, 2002).
Second Office Action for Patent Application No. 200480002190.5 issued by the Patent Office of the People's Republic of China (May 11, 2011).
Smirnov et al., "A Comparative Study of the Kinetics of Cytarabine Hydrolytic Deamination in Aqueous Solutions," Pharm. Chem. J. 34(8):451-454 (2000).
Srinivas R.V. et al., "Antiviral Activities of 9-R-2-Phosphonomethoxypropyl Adenine (PMPA) and Bis(isopropyloxymethylcarbonyl)PMPA against Various Drug-Resistant Human Immunodeficiency Virus Strains," Antimicrob. Agents Chemother, 42(6):1484-1487 (Jun. 1998) http://aac.asm.org/content/42/6/1484.full.pdf+html (retrieved Jan. 30, 2014).
Staszewski et al., NEJM, 1999, 341 5,1865-1873.
Staszewski S., et al., "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results," XIV International AIDS Conference, Barcelona, Spain, Abstracts, No. 9804:7-12 (2002) http://www.iasociety.org/Default.aspx?pageId=12&abstractId=9804 (retrieved Jan. 30, 2014).
Summons to attend Oral Proceedings EPO for Application No. 067731595.0 dated Jul. 9, 2013.
Teva Pharmaceutical Industries, Ltd, (Opponent), Opposition Brief against Israel Patent No. 169243 (dated Jul. 26, 2009).
Teva's Response to Patentee's Appeal, 5 pages, EP Pat. No. 1890681, EP Appl. No. 06773194.3 (mailed May 3, 2012).
Theory and Practice of Industrial Pharmacy, 3rd Edition, Lachman et al., Eds., Lea & Febiger, pp. 324-329 (1986).
Thoithi et al., "Investigation of the Kinetics of Degradation of Hexopyranosylated Cytosine Nucleosides Using Liquid Chronlatography," Nucleosides, Nucleotides & Nucleic Acids 19(1 &2):189-203 (2000).
Truvada Patient Information Leaflet, 33 pages (2008).
Van Rompay, et al., "9-[2-(Phosphonomethoxy)propyl]adenine therapy of established simian immunodeficiency virus infection in infant rhesus macaques," Antimicrob. Agents Chemother. 40:2586-2591 (1996) http://www.ncbi.nlm.nih.gov/pmc/articles/PMC163581/pdf/402586.pdf (Jan. 31, 2014).
Van Rompay, K. K., et al., "Virulence and reduced fitness of simian immunodeficiency virus with the M184V mutation in reverse transcriptase," J. Virology, 76(12):6083-6092 (2002) http://www.ncbi.nlm.nih.gov/pmc/articles/PMC136201/pdf/0196.pdf (retrieved Jan. 30, 2014).
Viread (Tenofovir Disoproxil Fumarate Tablets) Summary of Product Characteristics, EMEA, SmPC, 37 pages (Feb. 5, 2002).
Viread Label pp. 1-44 (2001).
Viread Patient Information Leaflet, 21 pages (2002).
Virji-Jeganathan, "BVV Stock Table Highlights," Bioventure View, 17(25): pp. 6-7 (Dec. 10, 2002).
Wang "FTC: A Potent and Selective Anti-HIV and Anti-HBV Agent Demonstrating Desirable Pharmacokinetic (PK Characteristics)," Abstracts of the IDSA, 36th Annual Meeting, Session 58, Poster 415, Hepatits A, B, and C in HIV-Infected Persons Friday, 4-6 pm (1998).
Wirth et al., "Maillard Reaction of Lactose and Fluoxetine Hydrochloride, a Secondary Amine," J. Pharm. Sci. 87(1):31-39 (1998).
Zalac et al., "Paracetamol-Propyphenazone Interaction and Formulation Difficulties Associated with Eutectic Formation in Combination Solid Dosage Forms," Chem. Pharm. Bull. 47(3):302-307 (1999).
Zao, Biokad Objection against the application of Eurasian Patent No. 015145 in the Russian Federation dated Jul. 10, 2013.
Affirmation of Andrew W. Williams in Support of Plaintiffs Merck, Sharp & Dohme Corp and Bristol-Myers Squib Company Co's Opening Claim Construction Brief and Exhibits Case No. 10-CV-01851 (Dec. 2, 2011).
Answer and Counterclaim filed by Teva Pharmaceuticals USA, Inc and Teva Pharmaceuticals Industries, Ltd. Case No. 09-CV-04463 (Aug. 10, 2009).
Answer to Amended Complaint filed by Teva Pharmaceuticals USA, Inc and Teva Pharmaceuticals Industries, Ltd. Case No. 10-CV-01796 (Jun. 29, 2011).
Complaint for Patent Infringement against Teva Pharmaceuticals USA, Inc and Teva Pharmaceuticals Industries, Ltd. filed by Gilead Sciences, Inc. Case No. 09-CV-04463 (May 8, 2009).
Declaration of Robin D. Rogers, Ph.D. In Support of Teva's Claim Constructions and Exhibits Case No. 10-CV-01851 (Jan. 13, 2012).
Declaration of Adam C. LaRock in Support of Plaintiffs' Claim Constructions and Exhibits filed by Gilead Sciences, Inc., Emory University Case No. 08-CV-10838 (Nov. 4, 2011).
Declaration of Adam C. LaRock in Support of Plaintiffs' Rebuttal Claim Constructions and Exhibits filed by Gilead Sciences, Inc., Emory University Case No. 08-CV-10838 (Dec. 16, 2011).
Declaration of Allan S. Myerson in Support of Plaintiffs' Claim Constructions and Exhibits filed by Gilead Sciences, Inc. Case No. 10-CV-01796 (Dec. 2, 2011).

(56) References Cited

OTHER PUBLICATIONS

Declaration of Andrew W. Williams in Support of Plaintiffs Merck, Sharp & Dohme Corp and Bristol-Myers Squib Company Co's Rebuttal Claim Construction Brief and Exhibits Case No. 10-CV-01851 (Jan. 13, 2012).
Declaration of Daniel P. Margolis in Support of Teva's Opening Claim Construction Brief and Exhibits filed by Teva Pharmaceuticals USA, Inc and Teva Pharmaceuticals Industries, Ltd. Case No. 10-CV-01796 (Dec. 2, 2011).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 08-CV-10838 (Dec. 16, 2011).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 10-CV-01796 (Jan. 13, 2012).
Declaration of Karen C. Shen in Support of Teva's Opening Claim Construction Brief and Exhibits Case No. 10-CV-01851 (Dec. 2, 2011).
Declaration of Michael J. Freno in Support of Teva's Opening Claim Construction Brief and Exhibits filed by Teva Pharmaceuticals USA, Inc and Teva Pharmaceuticals Industries, Ltd. Case No. 08-CV-10838 (Nov. 4, 2011).
Declaration of Natalie Lieber and Exhibits filed by Gilead Sciences, Inc. Case No. 10-CV-01796 (Dec. 2, 2011).
Declaration of Natalie Lieber in Support of Plaintiffs' Rebuttal Claim Constructions and Exhibits filed by Gilead Sciences, Inc. Case No. 10-CV-01796 (Jan. 13, 2012).
Declaration of Paul A. Bartlett in Support of Plaintiffs' Claim Constructions and Exhibits filed by Gilead Sciences, Inc., Emory University Case No. 08-CV-10838 (Nov. 4, 2011).
Declaration of Slaven Jesic in Support of Teva's Rebuttal Claim Construction Brief and Exhibits Case No. 10-CV-01851 (Jan. 13, 2012).
Defendants' Memorandum in Opposition to Plaintiffs Pretrial Memorandum filed by Teva Pharmaceuticals USA, Inc and Teva Pharmaceuticals Industries, Ltd. Case No. 10-CV-01796 (Jan. 28, 2013).
Defendants' Memorandum in Opposition to Plaintiffs' Pretrial Memorandum filed by Teva Pharmaceuticals USA, Inc and Teva Pharmaceuticals Industries, Ltd. Case No. 10-CV-01851 (May 24, 2013).
Defendants' Notice Pursuant to 35 U.S.C. § 282 filed by Merck, Sharp & Dohme Corp and Bristol-Myers Squib Company Co. Case No. 10-CV-01851 (May 22, 2013).
Defendants' Pretrial Memorandum filed by Teva Pharmaceuticals USA, Inc and Teva Pharmaceuticals Industries, Ltd. Case No. 10-CV-01851 (May 10, 2013).
Defendants' Pretrial Memorandum filed by Teva Pharmaceuticals USA, Inc and Teva Pharmaceuticals Industries, Ltd. Case No. 10-CV-01796 (Jan. 14, 2013).
Defendants' Proposed Findings of Fact and Conclusions of Law filed by Teva Pharmaceuticals USA, Inc and Teva Pharmaceuticals Industries, Ltd. Case No. 10-CV-01851 (May 10, 2013).
Defendants' Proposed Findings of Fact and Conclusions of Law filed by Teva Pharmaceuticals USA, Inc and Teva Pharmaceuticals Industries, Ltd. Case No. 10-CV-01796 (Jan. 14, 2013).
Defendants' Response to Plaintiffs' Request for Leave to Submit Supplemental Expert Witness Affidavit of Jerry L. Atwood, Ph.D. and Defendants' Request for Leave to Submit the Supplemental Declaration of Robin D. Rodgers, Ph.D. filed by Teva Pharmaceuticals USA, Inc and Teva Pharmaceuticals Industries, Ltd. Case No. 10-CV-01851 (May 30, 2013).
Excerpt of the Merck Veterinary Manual (Clarence M. Fraser et al. eds., 7th ed., 1991).
Excerpts from Daniel S. Kemp & Frank Vellaccio, Organic Chemisty (Worth Publishers, Inc. 1980).
Excerpts from K. Peter C. Vollhardt, Organic Chemistry (W.H. Freeman and Company 1987).
Excerpts of Teva Pharmaceuticals USA, Inc.'s Detailed Statement of the Factual and Legal Bases for Its Opinion That U.S. Patent Nos. 5,814,639, 5,914,331, 5,922,695, 5,935,946, 5,977,089. And 6,043,230 are Invalid, Unenforceable or Not Infringed by the Manufacture, Use or Sale of Its Emtricitabine & Tenofovir Disoproxil Fumarate Tablets, 200 mg/300 mg dated Jan. 28, 2010 ("2010 Detailed Statement").
Excerpts of Panel on Antiretroviral Guidelines for Adults and Adolescents, Department of Health and Human Services, Guidelines for the use of antiretroviral agents in HIV-1-infected adults and adolescents 1-167 (2011).
Excerpts of Teva Pharmaceuticals USA, Inc.'s Detailed Statement of the Factual and Legal Bases for Its Opinion That U.S. Patent Nos. 6,642,245 and 6,703,396 are Invalid, Unenforceable or Not Infringed by the Manufacture, Use or Sale of Its Emtricitabine & Tenofovir Disoproxil Fumarate Tablets, 200 mg/300 mg" dated Nov. 3, 2008 ("2008 Detailed Statement"); "Teva Pharmaceuticals USA, Inc.'s Detailed Statement of the Factual and Legal Bases for Its Opinion That U.S. Patent Nos. 6,642,245 and 6, 703,396 Are Invalid, Unenforceable or Not Infringed by the Manufacture, Use or Sale of Its Efavirenz/Emtricitabine/Tenofovir Disoproxil Fumarate Tablets, 600 mg/200 mg/300 mg" dated Mar. 30, 2009 ("2009 Detailed Statement"); and "Teva Pharmaceuticals USA, Inc.'s Detailed Statement of the Factual and Legal Bases for Its Opinion That U.S. Patent Nos. 5,814,639, 5,914,331, 5,922,695, 5,935,946, 5,977,089 and 6,043,230 are Invalid, Unenforceable or Not Infringed by the Manufacture, Use or Sale of Its Emtricitabine & Tenofovir Disoproxil Fumarate Tablets, 200 mg/300 mg dated Jan. 28, 2010 ("2010 Detailed Statement").
Excerpts of the Gilead Sciences, Inc., Q2, 2011 Earnings Results Conference Call and Webcast presentation, pgs. 16 & 19 (Jul. 26, 2011).
Excerpts of the Gilead Sciences, Inc., Q2, 2011 Earnings Results Conference Call and Webcast presentation, pg. 16-18 (Jul. 26, 2011).
First Amended Complaint for Patent Infringement filed by Gilead Sciences, Inc. Case No. 10-CV-01796 (Jun. 15, 2011).
Fischl, Margaret A. et al., Prolonged Zidovudine Therapy in Patients with Aids and Advanced Aids-Related Complex, 262 J.A.M.A. 2405 (1989).
Fourth Amended Answer filed by Teva Pharmaceuticals USA, Inc and Teva Pharmaceuticals Industries, Ltd. Case No. 08-CV-10838 (Oct. 17, 2011).
Fourth Amended Complaint for Patent Infringement against Teva Pharmaceuticals USA, Inc and Teva Pharmaceuticals Industries, Ltd. and Exhibits filed by Gilead Sciences, Inc., Emory University Case No. 08-CV-10838 (Oct. 3, 2011).
Harada, Shinji et al., *Infection of HTLV-IIIILAV in HTLV-I-Carrying Cells MT-2 and MT-4 and Application in a Plaque Assay*, 229 Science 563 (1985).
Hoong, Lee K. et al., Enzyme-Mediated Enantioselective Preparation of Pure Enantiomers of the Antiviral Agent 2',3'-Dideoxy-5-.fluoro-3'-thiacytidine (FTC) and Related Compounds, 57 J. Organic Chemistry 5563 (1992).
Larder, Brendan a. et al., HIV with Reduced Sensitivity to Zidovudine (AZT) Isolated During Prolonged Therapy, 243 Science 1731 (1989).
Merck, Sharp & Dohme Corp and Bristol-Myers Squib Company Co's Opening Claim Construction Brief Case No. 10-CV-01851 (Dec. 2, 2011).
Merck, Sharp & Dohme Corp and Bristol-Myers Squib Company Co's Rebuttal Claim Construction Brief Case No. 10-CV-01851 (Jan. 13, 2012).
Norton, Terry M. et al., Efficacy of Acyclovir Against Herpesvirus Infection in Quaker Parakeets, 52(12) Am. J. Vet. Res. 2007-09 (Dec. 1991).
Order signed by Judge Richard J. Sullivan Case No. 10-CV-01796 (Dec. 5, 2011).
Order signed by Judge Richard J. Sullivan Case No. 10-CV-01796 (Jan. 17, 2012).
Order signed by Judge Richard J. Sullivan Case No. 10-CV-01796 (Jan. 30, 2013).
Order signed by Judge Richard J. Sullivan Case No. 10-CV-01796 (Apr. 26, 2012).
Order signed by Judge Richard J. Sullivan Case No. 10-CV-01798 (May 26, 2010).
Order signed by Judge Richard J. Sullivan Case No. 08-CV-10838 (Dec. 19, 2011).
Order signed by Judge Richard J. Sullivan Case No. 10-CV-01851 (Jul. 19, 2013).
Order signed by Judge Richard J. Sullivan Case No. 10-CV-01851 (Jun. 5, 2013).

(56) References Cited

OTHER PUBLICATIONS

Order signed by Judge Richard J. Sullivan Case No. 10-CV-01851 (May 14, 2013).
Order signed by Judge Richard J.'Sullivan Case No. 10-CV-01851 (May 24, 2013).
Orders signed by Judge Richard J. Sullivan Case No. 10-CV-01796 (Jan. 18, 2013).
Plaintiffs Opening Claim Construction Brief filed by Gilead Sciences, Inc. Case No. 10-CV-01796 (Dec. 2, 2011).
Plaintiffs Opposition to Defendants' Pretrial Memorandum by Gilead Sciences, Inc. Case No. 10- CV-01796 (Jan. 28, 2013).
Plaintiffs Pretrial Memorandum filed by Gilead Sciences, Inc. Case No. 10-CV-01796 (Jan. 14, 2013).
Plaintiff's Proposed Findings of Fact and Conclusions of Law filed by Gilead Sciences, Inc. Case No. 10-CV-01796 (Jan. 14, 2013).
Plaintiffs' Opening Claim Construction Brief filed by Gilead Sciences, Inc., Emory University Case No. 08-CV-10838 (Nov. 4, 2011).
Plaintiffs' Opening Pretrial Brief filed by Merck, Sharp & Dohme Corp and Bristol-Myers Squib Company Co. Case No. 10-CV-01851 (May 10, 2013).
Plaintiffs' Proposed Findings of Fact and Conclusions of Law filed by Merck, Sharp & Dohme Corp and Bristol-Myers Squib Company Co. Case No. 10-CV-01851 (May 10, 2013).
Plaintiffs' Rebuttal Claim Construction Brief filed by Gilead Sciences, Inc., Emory University Case No. 08-CV-10838 (Dec. 16, 2011).
Plaintiffs' Rebuttal Claim Construction Brief filed by Gilead Sciences, Inc., Emory University Case No. 10-CV-01796 (Jan. 13, 2012).
Plaintiffs' Reply to Teva USA's Counterclaim filed by Gilead Sciences, Inc., Emory University Case No. 09-CV-04463 (Aug. 31, 2009).
Plaintiffs' Response to Defendants' Pretrial Memorandum filed by Merck, Sharp & Dohme Corp and Bristol-Myers Squib Company Co. Case No. 10-CV-01851 (May 24, 2013).
Request for Leave to Submit Supplemental Expert Witness Affidavit of Jerry L. Atwood, Ph.D. on behalf of Plaintiffs filed by Merck, Sharp & Dohme Corp and Bristol-Myers Squib Company Co. Case No. 10-CV-01851 (May 24, 2013).
Stella, Valentino J. et al., *Prodrugs and Site-Specific Drug Delivery*, 23 Journal of Medicinal Chemistry 1275 (1980).
Stipulation and Agreement Regarding U.S. Patent Nos. 5,922,965, 5,935,946, 5,977,089, and 6,043,230 Case No. 10-CV-01796 (Oct. 9, 2012).
Teva Pharmaceuticals USA, Inc and Teva Pharmaceuticals Industries, Ltd.'s Opening Claim Construction Brief Case No. 10-CV-01851 (Dec. 2, 2011).
Teva Pharmaceuticals USA, Inc and Teva Pharmaceuticals Industries, Ltd.'s Rebuttal Claim Construction Brief Case No. 10-CV-01851 (Jan. 13, 2012).
Teva Pharmaceuticals USA, Inc.'s Detailed Statement of the Factual and Legal Bases for Its Opinion That U.S. Patent Nos. 5,922,695., 5,935,946, 5,977,089, and 6,043,230 are Invalid, Unenforceable or Not Infringed by the Manufacture, Use or Sale Of Tenofovir Disoproxil Fumarate Tablets, 300 mg dated Jan. 25,2010 ("2010 Detailed Statement").
Teva's Opening Claim Construction Brief filed by Teva Pharmaceuticals USA, Inc and Teva Pharmaceuticals Industries, Ltd. Case No. 08-CV-10838 (Nov. 4, 2011).
Teva's Opening Claim Construction Brief filed by Teva Pharmaceuticals USA; Inc and Teva Pharmaceuticals Industries, Ltd. Case No. 10-CV-01796 (Dec. 2, 2011).
Teva's Rebuttal Claim Construction Brief filed by Teva Pharmaceuticals USA, Inc and Teva Pharmaceuticals Industries, Ltd. Case No. 08-CV-10838 (Dec. 16, 2011).
Teva's Rebuttal Claim Construction Brief filed by Teva Pharmaceuticals USA, Inc and Teva Pharmaceuticals Industries, Ltd. Case No. 10-CV-01796 (Jan. 13, 2012).
Transcript of Proceedings held on Apr. 26, 2012 Case No. 10-CV-01796.
Transcript of Proceedings held on Oct. 3, 3012, 2012 Case No. 10-CV-01796.
Written Opinion of the ISA for PCT/US2006/023222 (Feb. 23, 2007).
Yeni et al., "Antiretroviral Treatment for Adult HIV Infection in 2002," JAMA 288(2):222-235 (2002).
Yuan et al., "Degradation Kinetics of Oxycarbonyloxymethyl Prodrugs of Phosphonates in Solution," Pharm. Res. 18(2):234-237 (2001).
Zhang et al. "Phase transformation considerations during process development and manufacture of solid oral dosage forms" Adv Drug Del Reviews 56(30), 371-390 (2004).
"Graph," and "convolute of graphs,", cited as documents D54 and D55 in opposition proeedings of EP 04701819.7, Statement of Appeal Grounds filed Jun. 24, 2011.
"Lactose Anhydrous," p. 373 in Analytical Profiles of Drug Substances, vol. 20, Ed. Klaus Florey, Academic Press, Inc. (1990).
"Lactose," Handbook of Pharmaceutical Excipients, 3rd ed. Ed. A.H. Kibbe, American Pharmaceutical Association, pp. 276-285 (2000) pp. 276-285 (2000).
"New Uses for Tenofovir; More Questions about d4T," Project Inform Perspective 35:15-16 (2003).
Ait-Khaled, et al., "Zidovudine appears to prevent selection of K65R and L74V mutations normally selected by abacavir mono- or combination therapies not containing zidovudine" Antiviral Therapy, 2002, 7:S107 (Abstract).
Arimilli et al., "Nucleotide Analogues," U.S. Appl. No. 60/022,708, 40 pages (filed Jul. 26, 1996).
Arzneiformenlehre. Ein Lehrbuch für Pharmazeuten, List et al., Eds., Wissenschaftliche Verlagsgesellschaft mbH, pp. 79 and 477 (1985). An English translation is not readily available. Applicants believe this reference discloses that preparations with lactose can undergo the Maillard reaction with amines. Such preparations result in discolorations. Amines and reducing sugars may also form N-glycosylamines which may react further in a Maillard reaction.
BioWorld Today, "About BioWorld," 1 page, http://www.bioworld.com/servlet/com.accumedia.web.Dispatcher?next=aboutUs (2010).
Bloor, S., et al, "Patterns of HIV drug resistance in routine clinical practice; a survey of almost 12000 samples from the USA in 1999," Antiviral Therapy, 5 (Suppl. 3): 132.
Borroto-Esoda et al., "In vitro evaluation of the anti-HIV activitiy and metaboloc interactions of tenofovir and emtricitabine," Antiviral Therapy 11:377-384 (2006).
Brief Communication from EPO for Application No. 067731595.0 dated Nov. 10, 2013.
Brogan et al., "Cost-Effectiveness of Nucleoside Revers Transcriptase Inhibitor Pairs in Efavirenz-Based Regimens for Treatment-Naïve Adults with HIV Infection in the United States," Value in Health 14:657664 (2011).
Carpenter, C.C.J., et al., "Antiretroviral Therapy for HIV Infection in 1997: Updated Recommendations of the International Aids Society—USA Panel," The Journal of the American Medical Association 277(24) 1962-1969 (Jun. 25, 1997).
Castello and Mattocks, "Discoloration of Tablets Containing Amines and Lactose," J. Pharm. Sci. 106108 (Sep. 21, 2006).
Cherry, et al., "Mutations at codon 184 in simian immunodeficiency virus reverse transcriptase confer resistance to the (-) enantiomer of 23'-dideoxy-3,-thiacytidine. - Antimicrob.," Agents Chemother. 41:2763-2765(1997) http://aac.asm.org/content/41/12/2763.full.pdf+html (retrieved Jan. 29, 2014).
Cipla Ltd. (Opponent), Pre-Grant Opposition against Indian patent application 3383/DELNP/2005A (Dec. 11, 2007).
Communication and Annex from EPO for Application No. 067731595.0 dated Jul. 9, 2013.
Communication concerning Correction of the EP Specification for Patent Publication EP 1583542 (Application No. 04701819.7) issued by the European Patent Office (Jul. 22, 2008).
Communication from EPO for Application No. 067731595.0 dated Nov. 15, 2013.
Communication from EPO for Application No. 067731595.0 dated Dec. 4, 2013.

METHOD AND COMPOSITION FOR PHARMACEUTICAL PRODUCT

This application is a continuation of U.S. patent application Ser. No. 11/452,472, now abandoned, filed Jun. 13, 2006, which claims the benefit of U.S. patent application Ser. No. 60/771,353, filed Feb. 7, 2006 and U.S. patent application Ser. No. 60/690,010, filed Jun. 13, 2005, the disclosures of all of which are incorporated by reference as if fully set forth herein.

BACKGROUND OF THE INVENTION

This application relates to products for the treatment of viral infections, in particular HIV infections, using the known antiviral compounds efavirenz (tradename Sustiva, also known as EFV), emtricitabine (tradename Emtriva, also known as FTC) and tenofovir DF (disoproxil fumarate, also known as TDF) (tradename Viread, sold in combination with emtricitabine under the tradename Truvada).

The Truvada product is produced by wet granulation of emtricitabine and tenofovir DF (WO 04/64845), which under the circumstances produces a chemically stable dosage form. This product does not contain efavirenz.

HIV therapy using efavirenz as well as emtricitabine and tenofovir DF has been considered desirable. (hereafter "triple combination"; see WO 04/64845). Manufacturing a commercially viable triple combination product, however, would require that the final product meet stringent FDA requirements for bioequivalence to the commercial products, Viread (tenofovir disoproxil fumarate), Emtriva (emtricitabine), and Sustiva (efavirenz), and that the tablet be of suitable size for patients to easily swallow.

Initial efforts to simply combine the three drugs (active pharmaceutical intermediates, or APIs) into a unitary, essentially homogeneous composition manufactured by wet granulation failed to produce a chemically stable tablet. The tenofovir DF in this combination tablet was highly unstable and rapidly degraded in stability studies. The efavirenz formulation was unexpectedly incompatible with tenofovir DF, a result now attributed to the surfactant (sodium lauryl sulfate) found in the efavirenz portion of the formulation.

Another attempt was made to produce the triple combination, this time using a dry granulation of the three part combination and omitting the surfactant. This resulted in a tablet that failed to achieve bioequivalence with respect to efavirenz in human clinical trials. The peak efavirenz concentration in the blood stream and total drug exposure (Cmax and AUC) were both below the parameters determined for the commercial comparator, Sustiva (efavirenz) tablets. The inventors concluded that at least the surfactant in the triple combination (efavirenz/emtricitabine/tenofovir disoproxil fumarate) tablets was necessary to achieve bioequivalence to Sustiva.

Next, combination tablets were manufactured by wet granulating the efavirenz component with the surfactant and other excipients, separately manufacturing the Truvada component using dry granulation, mixing the granulates together, compressing the mixture into tablets, and then film-coating the tablets. Unexpectedly, this approach also failed to produce the desired bioequivalence in between the commercial product, Sustiva (efavirenz), and clinical trial material (i.e., proposed commercial triple combination product). A novel and inventive step was needed to overcome the shortcomings of more straight-forward approaches to a triple combination dosage form.

As described further in copending U.S. Ser. No. 60/771,279 (filed of even date and expressly incorporated herein by reference) the stability and bioequivalence objectives for the triple combination tablet ultimately were achieved in an exemplary embodiment by dry granulating the emtricitabine/tenofovir disoproxil fumarate component, wet granulating the efavirenz component and, rather than using the straight-forward process of simply combining the granulates, instead organizing the granulates to produce a multilaminate dosage form, one component containing the emtricitabine/tenofovir disoproxil fumarate element, the other containing the efavirenz element. This minimized the contact of the tenofovir DF with surfactant, yet maintained the efavirenz excipients and process features that contributed to achieving bioequivalence.

An additional obstacle to the triple combination dosage form was presented, and it is this problem that the present application is directed to solving. As noted above, simply combining the excipients present in the known commercial products, Truvada and Sustiva tablets, was undesirable because the resulting tablet would contain the entire excipient load of the known tablets and thus would be large for a single tablet and present a dosage form that was difficult to swallow and therefore inconvenient for patient use. It thus was an objective to prepare a highly concentrated preparation of emtricitabine and tenofovir DF, which by reducing the amount of excipients in the preparation, would contribute to an overall reduction in the size of the triple combination tablet. However, simply reducing the proportion of excipient to API and wet granulating in accord with the known process was not effective in producing a stable composition.

While the prior art reports the successful manufacture of chemically stable Truvada preparations (WO04/64845) by wet granulation, these preparations typically contain relatively low proportions of excipient to API, on the order of to 1:1. Wet granulation of a preparation in which the proportion of excipient had been reduced to manageable amounts for a triple combination tablet unexpectedly resulted in a chemically unstable preparation. Without being held to any particular theory of operation, the inventors believe that so much water is required in the wet granulation of efavirenz (which has relatively low solubility in comparison to emtricitabine and tenofovir DF) that the latter two APIs dissolve into a eutectic mixture. These dissolved APIs, when dried during granulation, form a glassy or amorphous product, which is chemically unstable in comparison to the crystalline API. In the prior process enough excipient is present to ameliorate the effect of the excess water is, but this was not feasible when the ratio of excipient to API is reduced to a level required for a manageable triple combination oral dosage form.

SUMMARY OF THE INVENTION

In accordance with this invention, a stable preparation of emtricitabine/tenofovir DF is provided by dry granulating a composition comprising a pharmaceutically acceptable excipient, tenofovir DF and emtricitabine. The omission of destabilizing amounts of water from the granulation process eliminates the disadvantageous formation of an emtricitabine/tenofovir DF eutectic mixture and enhances the stability of the resulting pharmaceutical product. The practice of the method of this invention produces a composition comprising dry granulated emtricitabine and tenofovir DF.

DETAILED DESCRIPTION OF THE INVENTION

Dry granulation is a well-known pharmaceutical manufacturing process per se. In general, API is combined with excipients and lubricant excipient and then compressed to form a mass. This mass typically is then comminuted or milled, then sieved to obtain the desired size of particle. The granular product is compressed into tablets, filled into capsules or otherwise formed into a unitary dosage form in conventional fashion. This invention at least in part is directed to the products produced by this process.

Compression into a mass is accomplished by conventional equipment. Typically, the API and excipients are passed through a roller compactor or chilsonator apparatus for compaction. However, other means for compacting, e.g., compaction into slugs (or "slugging"), the API/excipient mixture optionally are used. This in turn is comminuted or milled, and then optionally sieved to produce the desired size granules.

A dry granulated composition comprising emtricitabine and tenofovir DF is defined as the product of a dry granulation process. This composition essentially retains the crystalline APIs and is substantially free of dried eutectic emtricitabine/tenofovir DF. It typically will contain less than about 15% by weight dried eutectic mixture, ordinarily less than about 10% and generally less than about 5%. Dry granulated compositions include the direct product of dry granulation, i.e., dry granules per se, as well as products made from such granules including tablets, capsules, suppositories and other pharmaceutical dosage forms. Forming the dry granules into such physical forms substantially retains the character of the dry granular starting material and does not result in a substantial change in the properties of the granular component of the physical form presented.

Dry granulation is conducted in the absence of a destabilizing amount of water, "destabilizing" being that amount of liquid water that is capable causing degradation (defined infra) of tenofovir DF and/or emtricitabine. Ordinarily, no water at all is added during the dry granulation process.

Bound, entrained or absorbed water are commonly present in excipients. This water will not significantly adversely affect the stability of tenofovir DF and thus is not excluded from the invention. In general, liquid water (added or generated in situ) from any source, e.g., chemical reactions, condensation, entrained ice, or the like is to be excluded from the granulation. However, minor amounts of liquid water optionally are added during granulation. These typically would be less than about 5% by weight, ordinarily less than about 1% by weight, however the water is generated or supplied. Water is present in the final granulation product up to about 10% by weight (Karl Fischer), but preferably is less, as low as 0.1% by weight. However, permitted quantities of water may vary depending upon other factors in the granulation, e.g., excipient type, temperature and so forth. For example, if a hygroscopic excipient is included this will convert added water into a bound form. All that is necessary is that the water not result in degradation of tenofovir DF in the final product. In general, water is excluded both from the pregranulation stage (preparation of the composition to be used directly in the granulation) as well as during the granulation process itself.

Absence of water or "dry" does not mean the absence of liquid. Granulations with organic solvents are optionally conducted in accordance with this invention provided that destabilizing amounts of water are excluded.

Dry granulation results in a product that contains minimal amounts of water. The amount of water in the product granulate or dosage forms made there from are measured by loss on drying (LOD) or by the Karl Fischer method. The LOD of compositions of this invention are about 15%, about 10%, about 5% or typically less than about 3% by weight. The Karl Fischer water is about from 0.1 to 10% by weight, usually less than about 5% by weight, or less than about 2%. The amount of water in the final preparations, as opposed to the granulates, is a function of granulate water as well as minor amounts of water used during subsequent process steps such as coating. These amounts of water added in later steps than granulation generally will not affect the stability of the emtricitabine/tenofovir DF APIs, and therefore are subject to considerable permitted variation.

"Degradation" of tenofovir DF is the generation—in pharmaceutically unacceptable amounts—of at least one of the degradation products mono-POC PMPA, dimer or mixed dimer. "Degradation" of FTC is defined as the generation—in pharmaceutically unacceptable amounts—of FTU. These degradation products are shown below.

Mono-POC PMPA

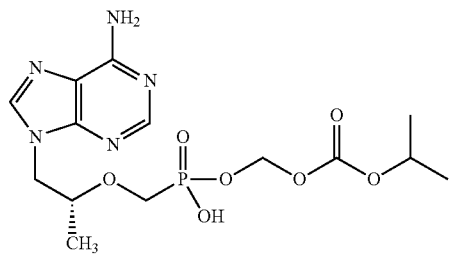

mono-POC PMPA

Dimeric. Degradation Products

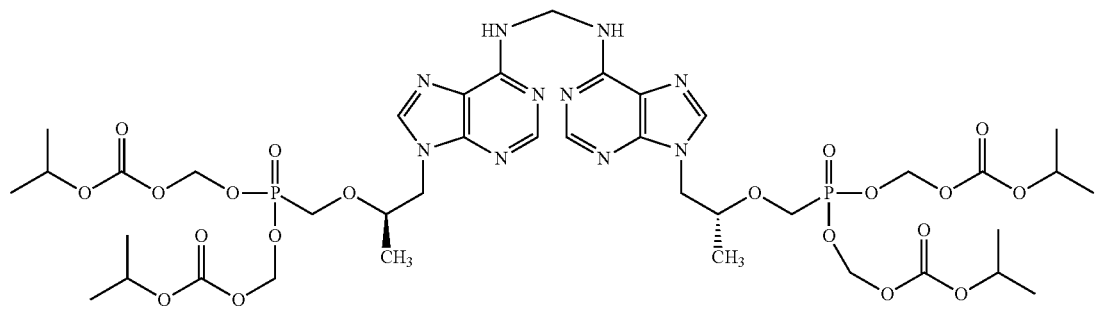

Dimer

-continued

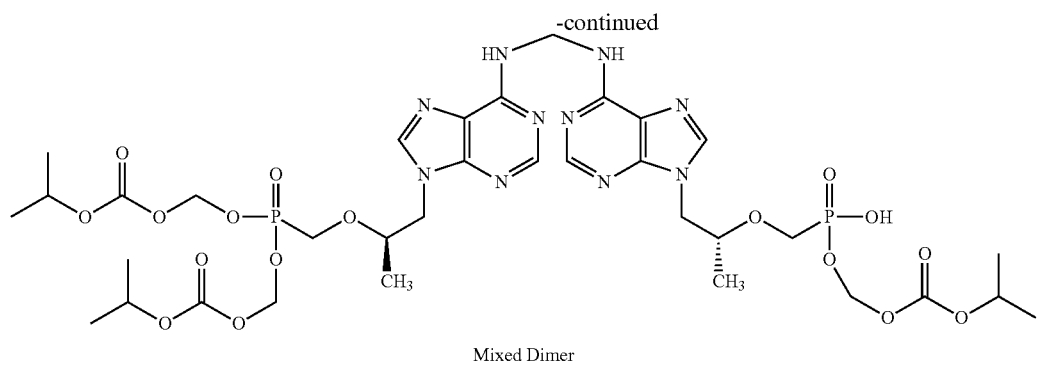

Mixed Dimer

FTU has the structure

A "pharmaceutically unacceptable amount" is defined as the following amounts of each degradation product. Degradation products optionally are assayed in either an absolute or incremental amount. The absolute or total amount of degradation product is simply the amount found in the test article. The incremental amount is the additional amount of degradation product appearing in the product over that which was present (if any) in the API starting material. Moreover, the amount of degradation product(s) optionally are measured at either or both of two points in time. One is the time of release into the marketplace. The other is after exposure to storage conditions under the conditions described below, i.e., the shelf life as set forth below.

Total amounts at release (first commercial sale)
  No more than about 3%, ordinarily about 1.5%, of mono-POC PMPA,
  No more than about 1%, ordinarily about 0.5% of Dimer,
  No more than about 0.5%, ordinarily about 0.25% of Mixed Dimer.
  Less than about 0.5%, ordinarily about 0.2% of FTU Total amounts at shelf life (storage under desiccant at 25° C./60% RH for 24 mo.).
  No more than about 10%, ordinarily about 5% of mono-POC PMPA,
  No more than about 2%, ordinarily about 1% of Dimer,
  No more than about 2%, ordinarily about 1% of Mixed Dimer.
  No more than about 4%, ordinarily about 2% of FTU Incremental amounts at release (first commercial sale)
  No more than about 2%, ordinarily about 0.5%, of mono-POC PMPA,
  No more than about 0.6%, ordinarily about 0.1% of Dimer,
  No more than about 0.3%, ordinarily about 0.05% of Mixed Dimer.
  Less than about 0.4%, ordinarily about 0.1% of FTU Incremental amounts at shelf life (storage under desiccant at 25° C./60% RH for 24 mo.)
  No more than about 9%, ordinarily about 4% of mono-POC PMPA,
  No more than about 1.6%, ordinarily about 0.6% of Dimer,
  No more than about 1.8%, ordinarily about 0.8% of Mixed Dimer.
  No more than about 3.9%, ordinarily about 1.9% of FTU.

The percentage of degradation products is the amount of degradation product as measured by HPLC retention time comparison. In the HPLC retention time comparison, the retention time of the main peaks observed in the tablets is required to be within 2% of the retention time of the main peaks in the a reference standard preparation containing efavirenz, emtricitabine, and tenofovir DF in an assay which has been shown to be specific for efavirenz, emtricitabine, and tenofovir DF. The percentage is determined by dividing the total amount of tenofovir DF plus the three degradation products into the amount of individual degradation product as determined by the HPLC assay.

Thus, for example, it is conceivable that a small amount of water might be desirably present during a dry granulation. This water might be added in the liquid form as an incidental solubilizing agent for an excipient included in the composition to be compressed. It also might be added bound to a hygroscopic excipient containing an unusually large amount of absorbed water. If the resulting product upon release did not contain more than the specified approximate limits of any one or more of the 4 contaminants listed under any of the 4 assay paradigms above, then the process concerned would still be considered a dry granulation process. Of course, the artisan may adopt more stringent standards (i.e., the amounts of some contaminants may be less than set forth above), but this will be a matter of choice and shall not limit the scope of this invention.

The manufacturing process described below is directed to one embodiment of the invention. Other embodiments will be well within the skill of the artisan. This embodiment entails the preparation of a triple combination tablet containing efavirenz, emtricitabine, and tenofovir DF. In this particular embodiment the last two drugs/excepients are segregated in a portion of the tablet, which is separate from, but in contact with, the portion of the tablet containing efavirenz/excipients. It will be understood, however, that the emtricitabine and tenofovir DF component of the tablet, which is an embodiment of this invention, optionally is manufactured for example as a stand-alone product and not necessarily in assembly with an efavirenz component. In this case, the emtricitabine/tenofovir DF dry granulation intermediate described below is optionally combined with other APIs or excipients, and compressed into tablets or conventionally processed into other conventional unitary dosage forms such as capsules, cachets, suppositories, or the like.

The manufacturing method for the triple combination tablet employs two separate granulation steps. The efavirenz final blend (efavirenz and excipients) was produced by a wet granulation process whereas emtricitabine, tenofovir DF, and suitable excipients were blended and dry granulated by a roller compaction process. The final blends were compressed into a bilayer tablet which in turn was film-coated with an immediate release coating.

Materials

The quantitative compositions of the efavirenz powder blend, FTC/TDF powder blend, and film-coated bilayer EFV/FTC/TDF tablets are listed in Table 1, Table 2, and Table 3, respectively. The quantities of efavirenz, emtricitabine, and tenofovir DF were adjusted for drug content factors (DCF) if the value was less than 0.99 with a concomitant reduction to the quantity of microcrystalline cellulose in each granulation.

TABLE 1

Quantitative composition of efavirenz powder blend

| Ingredient | % w/w of Total | Unit Formula (mg/tablet) |
|---|---|---|
| Efavirenz | 38.71 | 600.0 |
| Microcrystalline Cellulose, NF/EP | 11.52 | 178.6 |
| Hydroxypropyl cellulose, NF/EP | 2.48 | 38.4 |
| Sodium Lauryl Sulfate, USP/EP | 0.77 | 12.0 |
| Croscarmellose Sodium, NF/EP | 3.87 | 48.0 |
| Magnesium Stearate, NF/EP | 0.58 | 9.6 |
| Total for Tablet Core | 57.94 | 898.0 |

TABLE 2

Quantitative composition of FTC/TDF powder blend

| Ingredient | % w/w of Total | Unit Formula (mg/tablet) |
|---|---|---|
| Emtricitabine | 12.90 | 200.0 |
| Tenofovir Disoproxil Fumarate | 19.35 | 300.0 |
| Microcrystalline Cellulose, NF/EP | 5.77 | 89.5 |
| Croscarmellose Sodium, NF/EP[a] | 3.10 | 48.0 |
| Magnesium Stearate, NF/EP[a] | 0.94 | 14.5 |
| Total for Tablet Core | 42.06 | 652.0 |

[a]To be incorporated into both the intragranular and extragranular portions of the formulation during the manufacturing process.

TABLE 3

Quantitative composition of film-coated bi-layer EFV/FTC/TDF Tablets

| Ingredient | % w/w of Total | Unit Formula (mg/tablet) |
|---|---|---|
| Efavirenz Powder Blend | 57.94 | 898.0 |
| FTC/TDF Powder Blend | 42.06 | 652.0 |
| Total for Tablet Cores | 100.00 | 1550.0 |
| Opadry II Pink | 3.00 | 46.5 |
| Purified Water, USP/EP[a] | | |
| Total for Film-Coated Tablets | | 1596.5 |

[a]Water removed during film-coating process.

The excipients were all compendial grade materials:

Efavirenz Wet Granulation

Efavirenz was wet granulated using a Niro-Fielder PMA-400 equipment train. Efavirenz, microcrystalline cellulose and sodium lauryl sulfate (Table 1) were added to the PMA-400 and blended for 3 minutes. Croscarmellose sodium and hydroxypropyl cellulose (Table 1) were added to the pre-mix and blended for an additional 2 minutes. Purified water was added to form a suitable granulation followed by additional wet massing after water addition. Table 4 lists the summary of granulation parameters used for two representative lots and sub parts. All sub parts used a water to efavirenz ratio of 1.30 except for AB509 Mix C which used a 1.25 ratio of water to efavirenz.

TABLE 4

Efavirenz wet granulation process parameter summary

| Process | Parameter | AB507 | | | AB509 | | |
| | | Mix A | Mix B | Mix C | Mix A | Mix B | Mix C |
|---|---|---|---|---|---|---|---|
| Granulation | Total Water Added (kg) | 33.57 | 33.56 | 33.56 | 33.56 | 33.56 | 32.18 |
| | Ratio of Water:EFV | 1.30 | 1.30 | 1.30 | 1.30 | 1.30 | 1.25 |
| | Total Addition Time (Min:Sec) | 9:36 | 9:29 | 9:24 | 9:17 | 9:32 | 9:02 |
| | Final Impeller Power (% Load) | 10.4 | 9.8 | 8.5 | 11.3 | 11.3 | 9.9 |
| Wet Massing | Total Time (Min:Sec) | 4:00 | 3:00 | 3:00 | 2:00 | 1:15 | 2:00 |
| | Final Impeller Power (% Load) | 11.6 | 12.0 | 11.7 | 18.0 | 17.7 | 10.5 |
| Drying[a] | Inlet Temperature (° C.) | | 70 | | | 70 | |
| | Time (Hr:Min) | | 1:45 | | | 1:51 | |
| | Final Outlet Temp. (° C.) | | 50 | | | 50 | |
| | Final LOD (%) | | 0.3 | | | 0.8 | |

[a]Mixes A, B, and C for each lot were combined before drying.

In general, the wet granules were milled, then dried to an LOD less than or equal to 1.5%. The dried granules were milled and blended with magnesium stearate (Table 1).

The bulk density, particle size, and moisture content by LOD of the efavirenz granulations are listed in the first three lines of Table 5 (the B lot numbers are efavirenz products, the C lot numbers are emtricitabine/tenofovir DF). Particle size was determined by sifting 10-gram samples through 3-inch diameter screens using a sonic sifter (Model L3P, ATM Corporation, Milwaukee, Wis., USA). The following US Standard Mesh sizes (openings) were used: #20 (850 μm), #30 (600 μm), #40 (425 μm), #60 (250 μm), #80 (180 μm), and #250 (63 μm). The agitation and pulse were set at 7 and the sifting time was 5 minutes. The amount of powder retained on the sieves and the fines collector was determined by calculating the difference in weight before and after sifting. The geometric mean particle size was calculated by logarithmic weighting of the sieved distribution.

Bulk density was determined by filling a 100-mL graduated cylinder with sample and calculating the difference in weight between the empty and full graduated cylinder per unit volume. In typical embodiments the bulk density of the granules is about from 0.25 to 0.75 g/mL.

Moisture content measurements by loss on drying (LOD) were performed by heating a 2.5 g sample at 85° C. for 15 minutes using a heat lamp/balance system (Model LP16/PM400, Mettler-Toledo, Columbus, Ohio, USA).

The granulations had similar bulk densities (0.54 to 0.56 g/mL) and similar geometric mean particle size distributions (215 to 268 μm). The LOD values of the final blend were consistent from 0.98 to 1.80%. The individual sieve distributions for the efavirenz granulations are listed in Table 6.

TABLE 5

Summary of efavirenz powder blend and emtricitabine/tenofovir DF powder blend physical properties

| Gilead Lot Number | Geometric Mean Diameter Particle Size (μm) | Bulk Density (g/mL) | LOD (%) |
|---|---|---|---|
| AB507 | 247 | 0.56 | 1.80 |
| AB508 | 215 | 0.55 | 1.08 |
| AB509 | 268 | 0.54 | 0.98 |
| AC507 | 330 | 0.60 | 0.91 |
| AC508 | 344 | 0.60 | 1.02 |
| AC509 | 343 | 0.59 | 0.99 |

TABLE 6

Particle size distribution for efavirenz and FTC/TDF powder blends

| | % Weight Retained on Screen$^a$ US Standard Screen Size (mesh opening) | | | | | | |
|---|---|---|---|---|---|---|---|
| Gilead Lot No. | 20 (>850 μm) | 30 (600 μm) | 40 (425 μm) | 60 (250 μm) | 80 (180 μm) | 230 (63 μm) | pan (<63 μm) |
| AB507 | 5.9 | 10.9 | 16.2 | 22.2 | 11.4 | 22.6 | 10.9 |
| AB508 | 6.1 | 10.4 | 15.8 | 20.0 | 9.0 | 20.8 | 17.9 |
| AB509 | 9.6 | 13.3 | 17.4 | 20.1 | 8.9 | 17.2 | 13.3 |
| AC507 | 22.0 | 19.8 | 15.2 | 11.2 | 4.6 | 10.5 | 16.6 |
| AC508 | 22.1 | 20.1 | 15.4 | 11.6 | 5.1 | 10.6 | 14.9 |
| AC509 | 22.4 | 19.7 | 15.3 | 11.7 | 4.8 | 11.1 | 14.8 |

Emtricitabine/Tenofovir DF Dry Granulation

Emtricitabine, microcrystalline cellulose, tenofovir DF, and croscarmellose (Table 2) were blended in a 650 L tote bin using a Gallay blender for 10 minutes. Magnesium stearate (Table 2) was added and blended for an additional 5 minutes. This pre-blend was then transferred to a 320-L Matcon bin fitted with a cone valve discharging station to assist with material transfer into the roller compactor hopper.

The pre-blend was roller compacted using a Gerteis Macro-Pactor model 250/25/3 with 250 mm diameter by 50 mm wide smooth rolls. The roll gap thickness (2 mm), roll speed (10 rpm), compaction force (4 kN/cm), oscillating mill speed (75 rpm clockwise and counterclockwise), and oscillating mill screen opening (1.25 mm) were kept constant for all batches. The oscillating mill angle of rotation was also the same for all lots at 150° clockwise and 140° counterclockwise.

There was no material handling issues among all three batches while feeding into the roller compactor. The entire roller compaction process proceeded without any apparent sign of heat accumulation on the equipment, product build-up, or melting. The granulations then were blended with extragranular croscarmellose sodium (34% of total amount) and magnesium stearate (47% of total amount).

The particle size, bulk density, and LOD of the emtricitabine/tenofovir DF dry granulations were all similar for the three batches and are listed in Table 5 (bottom 3 compartments). The geometric particle sizes were very similar at from 330 to 344 μm. Bulk densities ranged from 0.59 to 0.60 g/mL. The final blend LOD values were consistent from 0.91 to 1.02%. The final powder blends have remarkably consistent physical properties.

The efavirenz and tenofovir DF granulations each have geometric mean particle sizes that optionally range about from 100 to 600 μm, bulk densities optionally ranging about from 0.1 to 1 g/mL and LOD values optionally ranging about from 0.1 to 5% by weight.

Final Blends

The mass of efavirenz granulation and extragranular magnesium stearate were adjusted appropriately based on the yield of emtricitabine/tenofovir DF dry granulation. Efavirenz granulation and emtricitabine/tenofovir DF dry granulation were blended in a 3 cubic foot V-blender for 10 minutes. Magnesium stearate was added and blended an additional 5 minutes. Samples of the final powder blend were taken from 10 different locations after blending and analyzed for blend uniformity. The efavirenz and emtricitabine/tenofovir DF final powder blends showed acceptable blend uniformity and homogeneity for all three active ingredients indicating the robustness of the formulation regardless of the particle size or bulk density of emtricitabine/tenofovir DF dry granulations and efavirenz granulations. The granulations and blending procedure would be satisfactory for the formulation on a larger scale.

Tablet Core Compression

Efavirenz/emtricitabine/tenofovir DF final powder blend was compressed into tablet cores using a Stokes Genesis Model 757, 41 station bilayer tablet press equipped plain-faced upper/embossed "123" lower, capsule-shaped (20.0 mm×10.4 mm) punches. The target mass of the tablet cores was 1550 mg. Samples of the core tablets were taken from a minimum of 20 equally spaced locations during the compression run and analyzed for content uniformity. In general, all powder blends compressed satisfactory on the rotary tablet press with respect to tablet hardness, friability, tablet thickness, tablet appearance, and tablet weight variation. The compression operation was performed at a rate of approximately 500 tablets/minute (12 rpm press speed) or approximately 0.8 kg/minute to deliver satisfactory tablet weight uniformity.

Tablet Film-Coating

Suitable film coatings are selected by routine screening of commercially available preparations. This activity is well within the skill of the ordinary artisan. Each lot of tablet cores was divided into two coating sub-lots that were film coated in a 48-inch Thomas Engineering COMPU-LAB coating pan using a dual-nozzle spraying system. All the tablet cores were film-coated using a 15% w/w aqueous coating suspension Opadry II pink, which was used within 24 hours of preparation. All tablet cores were coated to a target weight gain of 3.0% using a target spray rate of 180 g/min, which corresponds to a normalized spray rate of 1.5 to 2.3 g/min/kg tablets.

HPLC Assay for Degradation Products

Efavirenz/emtricitabine/tenofovir DF tablets (EFV/FTC/TDF tablets) are assayed by HPLC for EFV, FTC, and TDF using external reference standards. The degradation products of EFV, FTC, and TDF are determined by area normalization with the application of relative response factors, as appropriate. The identity of EFV, FTC, and TDF are confirmed by comparison of their retention times with those of the reference standards.

Standard And Sample Solution Preparation

Standard and Sample Solvent
25 mM Phosphate Buffer, pH 3
Weigh and transfer 3.4 g of potassium phosphate monobasic, anhydrous into a 1 L volumetric flask. Add about 800 mL of water and mix until dissolved. Adjust the pH to 3.0±0.1 with phosphoric acid, then dilute to volume with water.
Sample Solvent (40:30:30 25 mM Phosphate Buffer, pH 3:Acetonitrile:Methanol)

Combine 400 mL of 25 mM Phosphate Buffer, pH 3, 300 mL of acetonitrile, and 300 mL of methanol and mix. Allow to equilibrate to ambient temperature.

50:50 Acetonitrile:Methanol

Combine 500 mL of acetonitrile and 500 mL of methanol and mix. Allow to equilibrate to ambient temperature.

Standard Solution

Accurately weigh approximately 60 mg of EFV reference standard, 20 mg of FTC reference standard, and 30 mg of TDF reference standard and transfer into a 100 mL volumetric flask. Add approximately 80 mL of sample solvent (40:30:30) to the flask and mix or sonicate until dissolved. Dilute to volume with sample solvent (40:30:30) and mix well. The final concentration of each component is approximately 0.6 mg/mL of EFV, 0.2 mg/mL of FTC, and 0.3 mg/mL of TDF.

System Suitability Test Solutions

Sensitivity Check Standard

Prepare a 10 µg/mL FTU stock solution by accurately weighing out approximately 10 mg of the FTU authentic substance into a 100 mL volumetric flask. Add sample solvent (40:30:30) to approximately 80% of volume and mix or sonicate until dissolved. Dilute to volume with sample solvent (40:30:30) and mix well. Pipet 10 mL of this solution into a 100 mL volumetric flask. Dilute to volume with sample solvent (40:30:30) and mix well.

Prepare the sensitivity check standard containing 0.2 mg/mL of FTC and 0.2 µg/mL of FTU (0.10% relative to FTC). Accurately weigh out 20 mg FTC into a 100 mL volumetric flask. Using a Class A pipet, transfer 2.0 mL of the FTU stock solution into the same flask. Add additional sample solvent (40:30:30) to the flask and mix or sonicate until dissolved. Dilute to volume with sample solvent (40:30:30) and mix well. Alternately, 2.0 mL of the 10 µg/mL FTU stock solution may be added to the standard solution prior to diluting to volume.

Sample Preparation for EFV/FTC/TDF Tablets

The strength and degradation product content of EFV/FTC/TDF tablets is determined by the analysis of a composite solution prepared from ten tablets.

The final concentration of each component in the sample solution is approximately 0.6 mg/mL of EFV, 0.2 mg/mL of FTC, and 0.3 mg/mL of TDF.

a) Place ten tablets into a 1 L volumetric flask and add 400 mL 25 mM phosphate buffer, pH 3 to the volumetric flask.
b) Mix by stirring vigorously for about 75 minutes.
c) Add 50:50 acetonitrile:methanol to the flask to approximately 2 cm below the volume mark.
d) Equilibrate the solution to ambient temperature by mixing for an hour. Dilute to volume with 50:50 acetonitrile:methanol. Mix well by inverting the flask or stirring with a magnetic stir bar.
e) Using a 0.45 µm syringe filter with a syringe, filter approximately 10 mL of step (d) for the next dilution. Discard the first 2 mL of filtrate.
f) Using a Class A pipet, transfer 5.0 mL of the filtrate from step (e) into a 50 mL volumetric flask and dilute to volume with sample solvent (40:30:30). Mix well.

CHROMATOGRAPHY

1. An HPLC equipped with a UV detector and an electronic data acquisition system is used.
2. An HPLC column, 4.6 mm i.d. by 250 mm long, packed with C12 reversed phase, 4 µm particle size, 80 Å pore size material is used.
3. Mobile phase buffer: Prepare a 20 mM ammonium acetate buffer, pH 4.6; adjust pH with acetic acid as needed.
4. Mobile phase gradient: Elute with Mobile Phase Buffer: acetonitrile from 99:1 to 1:99 over 67 minutes.
5. Peak detection: UV at 262 nm
6. Injection volume: 10 µL.

Under the stated chromatographic conditions, the retention times of the FTC, TDF and EFV peaks are typically 11, 33, and 50 minutes, respectively Injection Sequence Inject the sample solvent at least twice as a blank to ensure that the column is equilibrated and to identify any potential artifact peaks.

Inject the sensitivity check standard or standard solution containing approximately 0.10% MU to measure the sensitivity of detection.

Inject five replicates of standard solution 1 (R1), followed by a single injection of standard solution 2 (R2). Calculate the theoretical plates and tailing factors from the standard solution injections.

For identity, strength, and degradation product determination, perform duplicate injections of the sample solution.

All sample solutions must be bracketed by standard solution injections. Generally, not more than ten sample solution injections between bracketing standard injections is recommended.

System Suitability

Theoretical Plates and Tailing Factor

Calculate the number of theoretical plates (N) and the tailing factors (T) for the EFV, FTC, and TDF peaks from the Standard Solution chromatogram. The formulas for N and T detrmination are defined in the current United States Pharmacopeia. The values of these parameters must conform to the criteria : N ≤40,000 and 0.8≤S≥T 2.0.

Sensitivity Check

The sensitivity check will utilize the FTU peak in the sensitivity check standard present at approximately 0.10%. Calculate the area percent of the FTU peak with the appropriate RRF (listed in Table 2) applied for the sensitivity check standard using the calculation for percent individual degradation product. Compare this result to the theoretical percent of FTU for the sensitivity check standard as follows:

$$\text{Sensitivity} = \frac{FTU_{Determined}}{FTU_{Theoretical}}$$

Where: $FTU_{Determined}$=area percent of FTU determined for the sensitivity check standard or standard solution $FTU_{Theoretical}$ theoretical area percent of FTU for the sensitivity check standard or standard solution The sensitivity must be between 0.70-1.30.

Evaluation and Calculations

Identification of Degradation Products

Employ the appropriate detection parameters (such as peak threshold, minimum peak area, etc.) to allow detection of peaks present at 0.05% or less. Identify the impurities and degradation products of EFV, FTC, and TDF present in the chromatograms of the sample solution injections by noting the relative retention times (RRT) of the observed secondary peaks, discounting any peaks not related to the sample. Only degradation products are quantified. Calculate the average of the results from all sample solution injections to the nearest 0.01%. In cases where the degradation product was not detected or was below the threshold of integration in one injection and/or sample, use only the quantified results in the calculation (i.e., do not treat as a zero value).

$$RRT = \frac{\text{retention time of the secondary peak}}{\text{retention time of the tenofovir disoproxil peak}}$$

The RRTs and the relative response factor (RRF) values of the potential impurities and degradation products for EFV are shown in Table 1, and the degradation products are shown in bold-face. The impurities and degradation products for FTC are shown in Table 2, and the degradation products are in bold-face. The impurities and degradation products for TDF are shown in Table 3, and the degradation products are in bold face.

As the RRT may vary, the identity of impurities and degradation products may be confirmed by comparison to authentic substances (or to impurity and degradation product peaks in the reference standard), if required.

Degradation Product Content Determination

Quantification of FTC Degradation Products

Determine the level of each degradation product of FTC observed in the chromatograms of the sample solution injections using the following formula:

$$\text{Degradation Product (\%)} = \frac{I}{TPA} \times RRF \times 100$$

Where: I=Area of the degradation product peak
  IPA=Total peak area (area of FTC and all related degradation products, excluding impurities and artifacts), corrected by RRF
  RRF=Relative response factor with respect to FTC Quantification of TDF Degradation Products Determine the level of each degradation product of TDF observed in the chromatograms of the sample solution injections using the following formula:

$$\text{Degradation Product (\%)} = \frac{I}{TPA} \times RRF \times 100$$

Where: I=Area of the degradation product peak or unassigned peak
  TPA=Total peak area (area of the TDF main peak, all related degradation products, and all unassigned peaks, excluding impurities and artifacts), corrected by RRF
  RRF=Relative response factor with respect to TDF Results And Reporting
Degradation Product Content
  Report individually the average of the results for each degradation product observed to the nearest 0.01%. Report the total degradation product content of EFV, FTC, and TDF respectively to the nearest 0.1%, as the sum of the average levels of all degradation product peaks observed. For degradation products found at levels less than 0.05%, report their levels as trace and do not include their levels in the calculation of total degradation product content.

References
United States Pharmacopeia <621>
Pharmacopeial Forum 26(4) 2000

TABLE 1

EFV related impurities and degradation products

| EFV Related Compound | Approximate RRT[a] | RRF[b] |
|---|---|---|
| SD-573[c] | 1.46 | 0.5 |
| SR-695[d] | 1.50 | |
| EFV | 1.50 | |
| SP-234 | 1.57 | |
| SW-965 | 1.60 | |
| SE-563 | 1.73 | |
| SM-097[c] | 1.83 | 0.5 |

[a]Approximate RRTs, and the values are relative to the TDF peak
[b]RRFs for EFV related degradation products are relative to EFV
[c]EFV related degradation products
[d]SR-695 elutes before EFV (approximately 0.1 min separation)
Degradation products are marked in bold face

TABLE 2

FTC related degradation product

| FTC Related Compound | Approximate RRT[a] | RRF[b] |
|---|---|---|
| FTC | 0.33 | |
| FTU[c] | 0.38 | 0.7 |

[a]Approximate RRTs, and the values are relative to the TDF peak
[b]RRFs for FTC related degradation products are relative to FTC
[c]FTC related degradation products

TABLE 3

Tenofovir DF related degradation products

| TDF Related Compound | Impurity Number | Approximate RRT[a] | RRF[b] |
|---|---|---|---|
| mono-POC PMPA[c] | 3 | 0.47 | 0.6 |
| Mixed Dimer[c] | 13 | 0.98 | 1.0 |
| TDF | | 1.00 | |
| Dimer[c] | 14 | 1.34 | 0.9 |

[a]Approximate RRTs, and the values are relative to the TDF peak
[b]RRFs for TDF related degradation products are relative to TDF
[c]TDF related degradation products

What is claimed:

1. A method comprising granulating a composition comprising emtricitabine and tenofovir DF without contacting the composition with a destabilizing amount of liquid water.

2. The method of claim 1 wherein liquid water is not combined with the composition prior to or during granulation.

3. The method of claim 1 wherein the composition further comprises at least one pharmaceutically acceptable excipient.

4. The method of claim 1 wherein granulation comprises aggregating the composition and comminuting it to desired dimensions.

5. The method of claim 4 wherein the aggregation is accomplished by slugging or roller compaction.

6. The method of claim 4 wherein the composition is sieved to recover granules of the desired dimensions.

7. The method of claim 6 wherein the granules are retained by a 1.25 mm mesh.

8. The method of claim 3 wherein the excipient is a lubricant.

9. The method of claim 8 wherein the lubricant is an alkali metal salt of a C8-C18 fatty acid.

* * * * *